(12) United States Patent
Jenkins et al.

(10) Patent No.: US 6,710,166 B1
(45) Date of Patent: Mar. 23, 2004

(54) 41 KDA CRYPTOSPORIDIUM PARVUM OOCYST WALL PROTEIN

(75) Inventors: Mark C. Jenkins, Davidsonville, MD (US); Ron Fayer, Columbia, MD (US); James Trout, Columbia, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 66 days.

(21) Appl. No.: 09/888,501

(22) Filed: Jun. 26, 2001

Related U.S. Application Data

(62) Division of application No. 09/451,117, filed on Nov. 30, 1999, now Pat. No. 6,277,973.

(51) Int. Cl.$^7$ .............................................. A61K 38/00
(52) U.S. Cl. ................. 530/300; 424/151.1; 424/191.1; 424/269.1; 435/7.22; 435/342
(58) Field of Search ........................... 424/151.1, 191.1, 424/269.1; 435/7.22, 342; 530/300, 350

(56) References Cited

PUBLICATIONS

Harlow et al. Antibodies: A laboratory manual. Cold Spring Harbor Laboratories Publications, Cold Spring Harbor, NY ed. Harlow et al., p. 76.*
Ngo et al. The Protein Folding Problem and Tertiary Structure Prediction. (1994) pp. 492–495.*
Bork, Powers and pitfalls in sequence analysis: the 70% hurdle. Genome Research (2000) vol. 10, pp. 398–400.*
Skolnick et al. From genes to protein structure an function: novel applications of computational approaches in the genomic era. Trends in Biotechnology (2000) vol. 18, No. 1, pp. 34–39.*
Bowie et al. Deciphering the message in protein sequences: tolerance to amino acid substitutions. 1990, Science (1990) vol. 247, pp. 1306–1310.*
Lazar et al. Transforming growth factor alpha: mutation of Asp 47 and Leu 48 results in different biological activities. Molecular and Cellular Biology (1988) vol. 8, pp. 1247–1252.*
Michael J. Arrowood, "Diagnosis", in *Cryptosporidium and Cryptosporidiosis*, R. Fayer, Ed. CRC Press, New York, NY, Chapter 2, pp. 43–64, 1997.
Michael W. Riggs, "Immunology: Host Response and Development of Passive Immunotherapy and Vaccines", in *Crytosporidium and Cryptosporidiosis*, R. Fayer, Ed., CRC Press, New York, NY, Chapter 6, pp. 43–64, 1997.
Frost et al., "Comparisons of ELISA and Western Blot Assays for Detection of Cryptosporidium", *Epidemiol. Infect.*, vol. 121, pp. 205–211, 1998.

Garcia et al., "Evaluation of Nine Immunossay Kits (Enzyme Immunossay and Direct Fluorescence) for Detection of *Giardia lamblia* and *Cryptosporidium parvum* in Human Fecal Specimens", *J. Clinical Microbiology*, vol. 35(6), pp. 1526–1529, 1997.
Graczyk et al., "Evaluation of Commercial Enzyme Immunoassay (EIA) and Immunofluorescent Antibody (IFA) Test Kits for Detection of Cryptosporidium Oocysts of Species Other Than *Cryptosporidium Parvum*", *Am. J. Trop. Med. Hyg.*, vol. 54(3), pp. 274–279, 1996.
Ignatius et al., "Efficacy of Different Methods for Detection of Low *Cryptosporidium parvum* Oocyst Numbers of Antigen Concentrations in Stool Specimens", *Eur. J. Clin. Microbiol. Infect. Dis.*, vol. 16, pp. 732–736, 1997.
Kehl et al., "Comparison of Four Different Methods for Detection of Cryptosporidium Species", *J. Clinical Microbiology*, vol. 33(2), pp. 416–418, 2/95.
Lorenzo et al., "*Cryptosporidium parvum* Oocyst Antigens Recognized by Sera from Infected Asymptomatic Adult Cattle", *Veterinary Parasitology*, vol. 60, pp. 17–25, 1995.
Nina et al., "Comparative Study of the Antigenic Composition of Oocyst Isolates of *Cryptosporidium parvum* from Different Hosts", *Parasite Immunology*, vol. 14, pp. 227–232, 1992.
Peeters et al., "*Cryptosporidium parvum* in Calves: Kinetics and Immunoblot Analysis of Specific Serum and Local Antibody Responses (Immunoglobulin A[IgA], IgG, and IgM) after Natural Experimental Infections", *Infection and Immunity*, vol. 60(6), pp. 2309–2316, 6/92.
Perryman et al., "A Cloned Gene of *Cryptosporidium parvum* Encodes Neutralization–Sensitive Epitopes[1]", *Molecular and Biochemical Parasitology*, vol. 80, pp. 137–147, 1997.
Reperant et al., "Major Antigens of *Cryptosporidium parvum* Recognised by Serum Antibodies from Different Infected Animal Species and Man", *Veterinary Parasitology*, vol. 55, pp. 1–13, 1994.
Tilley et al., "*Cryptosporidium parvum* (Apicomplexa: Cryptosporidiidae) Oocyst and Sporozoite Antigens Recognized by Bovine Colostral Antibodies", *Infection and Immunity*, vol. 58(9), pp. 2966–2971, 9/90.

* cited by examiner

*Primary Examiner*—James Housel
*Assistant Examiner*—Ulrike Winkler
(74) *Attorney, Agent, or Firm*—John D. Fado; Evelyn M. Rabin

(57) ABSTRACT

Recombinant proteins have been developed for the immunization of animals against cryptosporidiosis. The proteins are effective for the immunization of a variety of animals against *Cryptosporidium parvum*, particularly for the production of hyperimmune colostrum that may be used to confer passive immunity against the parasite. Isolated DNA sequences which encode these proteins have also been developed. The DNA sequences may be inserted into recombinant DNA molecules such as cloning vectors or expression vectors for the transformation of cells and the production of the proteins.

5 Claims, 12 Drawing Sheets

```
AATTTCTTCTTTTATGATGATTCTAAAAAGTATGAGGGAGGATTATTAAAAAAAGAAGGT      60
 N  F  F  Y  D  D  S  K  K  Y  E  G  G  L  L  K  K  E  G

TATGATGGTTGTACAGTAGTTGGTAGTGATTGTTTATGTTGGAGATGTTATTTCAATCAA     120
 Y  D  G  C  T  V  V  G  S  D  C  L  C  W  R  C  Y  F  N  Q

AGACCATTTTTTGAGGAGATGGACTATTCTAGGATTCCAATTTCTTCTGAGGTTATTTGT     180
 R  P  F  F  E  E  M  D  Y  S  R  I  P  I  S  S  E  V  I  C

GGATTATTGAATGGAATGGAATATTGTATTTGTAAATGTGATGAATTGGATATATTATTA     240
 G  L  L  N  G  M  E  Y  C  I  C  K  C  D  E  L  D  I  L  L

GAAAGATGGAATCCATTTTTGCTTTATAAATTTGAGCAGGAATATTTAAAGAATGGAGCA     300
 E  R  W  N  P  F  L  L  Y  K  F  E  Q  E  Y  L  K  N  G  A

ATTTTAATGGATAATAATATTGGAATACTTGTAAATAATACAATGGTAGGTATTGGTAAA     360
 I  L  M  D  N  N  I  G  I  L  V  N  N  T  M  V  G  I  G  K

AGGATGAATACTACTCAATCAATGGAAGTTACTGATACTAATATTGGTAATATGAGTGGT     420
 R  M  N  T  T  Q  S  M  E  V  T  D  T  N  I  G  N  M  S  G

ATTATTACATCTAGTGGTGATTCTATAGCTGTTACTAATAATCTTAATGGTAATAATAAT     480
 I  I  T  S  S  G  D  S  I  A  V  T  N  N  L  N  G  N  N  N

AGTAATAGTAATATTGGATCAGGAAATTTTATACCAGTTGGTACTTGTTCTTCTACTAGT     540
 S  N  S  N  I  G  S  G  N  F  I  P  V  G  T  C  S  S  T  S

ATTGGTAATAGTAATGGTGTTGCTTTTACTGCTATTCATCCTAATAATAACAATAGCAAT     600
 I  G  N  S  N  G  V  A  F  T  A  I  H  P  N  N  N  N  S  N

AATATTAATAATAATAATAATAATAATAGTAATACCACTCTTACTACTGTTGCTACTAAT     660
 N  I  N  N  N  N  N  N  N  S  N  T  T  L  T  T  V  A  T  N

GCTAATATTACTACTAATACTACTAATACTACTACTACTACTACTAATAATAATAATAAT     720
 A  N  I  T  T  N  T  T  N  T  T  T  T  T  T  N  N  N  N  N

AATAATAATAATAATAATTC                                              740
 N  N  N  N  N  N
```

FIG. 2

41 KDA *CRYPTOSPORIDIUM PARVUM* OOCYST WALL PROTEIN

This is a divisional of application Ser. No. 09/451,117, filed Nov. 30, 1999, now U.S. Pat. No. 6,277,973, which is herein incorporated by reference in its entirety.

BACKGROUND OF THE INVENTION

1. Field of the Invention

*Cryptosporidium parvum* is a protozoan parasite that has been implicated in numerous outbreaks of diarrheal disease in the human population. This invention relates to an isolated 41 kDa protein, CP41, specific for *C. parvum*; recombinant CP41(rCP41) proteins: a recombinant 36 kDa protein and a recombinant 28 kDa protein, both of which are specific for *C. parvum*; and the nucleic acid sequences which encode these proteins. The DNA which encodes CP41 and rCP41 can be used to specifically identify *C. parvum* oocytes through RT-PCR. The isolated and recombinant proteins can be used as reagents to detect antibodies in the serum of infected individuals, to make monoclonal antibodies that are specific for the native 41 kDa protein which specifically identifies *C. parvum* and thus distinguishes *C. parvum* from other Cryptosporidium species, to generate hyperimmune serum or colostrum for use in enhancing the anti-cryptosporidial response of young or immunocompromised individuals, and in vaccine development, to protect individuals from Cryptosporidium infection.

2. Description of the Relevant Art

Cryptosporidium is a protozoan that can cause acute, severe, self-limited disease in immunocompetent individuals and severe chronic diarrhea in immunocompromised individuals. The young and immunosuppressed are at particularly high risk. Worldwide, there is a much higher prevalence in children than in adults (Kehl et al. 1995. *J. Clin. Micro.* 33 (2): 416–418. Although in most individuals the disease is self-limiting and protective immunity develops after a primary infection, cryptosporidiosis is a major cause of death in immunodeficient hosts such as persons afflicted with AIDS. Development normally takes place in the intestinal epithelium and the transmissible stage, the oocyst, is excreted in the feces. In immunocompromised patients, cryptosporidiosis is not necessarily self-limiting and sites other than the small intestine, such as the respiratory tract, stomach, liver, pancreas, gall bladder, appendix, colon, rectum, and conjunctiva of the eye, may be affected (Fayer et al. 1997. In *Cryptosporidium and Cryptosporidiosis*, R. Fayer, Ed., CRC Press, New York, N.Y., page 29). Cryptosporidiosis is also a major disease of dairy and beef calves in the United States. Although a number of species of Cryptosporidium have been described, only *C. parvum* causes disease in both humans and calves.

Over the last decade, this protozoan parasite has been implicated in numerous outbreaks of diarrheal disease in the human population. The largest outbreak reported to date was almost five years ago in Milwaukee, Wis. where greater than 400,000 people showed clinical signs of cryptosporidiosis. The source of the parasite was traced to contaminated drinking water supplied by a municipal water treatment utility. Such widespread occurrence of Cryptosporidium oocysts in raw and treated drinking water supplies throughout the USA has raised concern that low-level endemic waterborne Cryptosporidium infections may occur commonly.

Cryptosporidium is transmitted through animal contact, person-to-person contact, and contaminated food and water.

The *C. parvum* infection is initiated by the ingestion of oocysts, the excystation of oocysts with release of sporozoites and the invasion of gut epithelial cells by sporozoites. Thereafter, the intracellular forms mature and release new daughter merozoites which reinvade the gut epithelial cells. *C. parvum* also has a sexual cycle. The sexual cycle of *C. parvum* also occurs in the gut and results in the production of sporulated oocysts, some of which may excyst before being shed. In persistent infection of an immunocompromised host, both the merozoite and the endogenously produced sporozoite may contribute to the ongoing invasion by *C. parvum*. Cryptosporidium spp. are resistant to standard disinfection processes and remain infectious for long periods of time in the environment at a wide range of temperatures. This resistance is imparted by the hard outer covering of the oocyst wall that surrounds the infectious stage of the parasite, i.e., sporozoites.

The detection of *Cryptosporidium parvum* oocysts in environmental samples usually relies on one of three different techniques—vital dye staining (e.g., Modified Ziehl-Neelsen acid fast staining), direct or indirect immunofluorescence staining (IFA), or enzyme immunoassay (EIA) using Cryptosporidium-reactive antibodies. Differences in the relative sensitivities of these assays have been noted (Garcia et al. 1997. *J. Clin. Micro.* 35 (6): 1526–1529; Graczyk et al. 1996. *Am. J. Trop. Med. Hyg.* 54(3): 274–279; Ignatius et al. 1997. *Euro. J. Clin. Micro. Inf. Dis.* 16: 732–736; and Kehl et al. 1995. *J. Clin. Microbiol.* 33: 416–418). The majority of immunocompetent patients, when initially symptomatic, have large numbers of oocysts present in their stools and their condition can be confirmed with a number of procedures; however, as the acute infection resolves, the patient becomes asymptomatic and the number of oocysts dramatically decreases (Garcia et al. 1997, supra). Low numbers of oocysts makes identification of *C. parvum* as the causative agent difficult. The high sensitivity of anti-Cryptosporidium monoclonal antibodies (mAbs) most certainly aids detection of Cryptosporidium in fecal or environmental samples; however, their use does not ensure the specific detection of *C. parvum*, the only species that represents potential public health threats. Cryptosporidium oocysts shed by a variety of captive and wild homoiothermal and poikilothermal animals contaminate the surface water and water supply. In the absence of *C. parvum*-specific mAbs, such oocysts can be misinterpreted as *C. parvum* oocysts potentially pathogenic for humans based on their identification as Cryptosporidium oocysts by crossreactive antibodies, i.e., antibodies that react with more Cryptosporidium species than *C. parvum* (Graczyk et al. 1996. *Am. J. Trop. Med. Hyg.* 54(3): 274–279). Similarly, diarrhea in patients may be inaccurately diagnosed as resulting from *C. parvum* under circumstances where an organism other than *C. parvum* is the causative agent and the patient carried Cryptosporidium oocysts (not *C. parvum*) from contacts not related to the diarrheal disease, i.e., environmental contacts. This problem is of particular concern for water treatment utilities that must monitor the efficiency of filtration processes and the contamination level of treated water destined for human consumption. None of the available immunoassays can differentiate *C. parvum* from other species of Cryptosporidium that are not infectious for mammals. The inability to sensitively detect and differentiate Cryptosporidium at the level of species or subspecies (strain) is a recognized constraint on our understanding of the natural history, epidemiology, and zoonotic potential of Cryptosporidium isolates and therefore makes the assessment of the public health risk posed by oocyst contamination of water or foods difficult (M. J. Arrowood. 1997. In *Cryptosporidium and Cryptosporidiosis*, R. Fayer, Ed., CRC Press, New York, N.Y., page 56).

Confirmatory diagnosis of cryptosporidiosis in patients is often carried out by assaying sera for recognition of specific Cryptosporidium antigens (Frost et al. 1998. *Epidemiol. Infect.* 121: 205–211). Several low molecular weight *C. parvum* oocyst antigens, such as 15 kDa, 17 kDa, and 23 kDa proteins, appear to be useful for identifying the presence of Cryptosporidium. The immunogenicity of 15, 17, and 23 kDa antigens and somewhat higher $M_r$ antigens (e.g., 32, 47 kDa) has been observed in other mammalian species infected or immunized with *C. parvum* oocysts (Lorenzo et al. 1995. *Vet. Parasitol.* 60: 17–25; McDonald et al. 1992. *Parasite Immunol.* 14: 227–232; Nina et al. 1992. *Infect. Immun.* 60: 1509–1513; Peeters et al. 1992. *Infect. Immun.* 60: 2309–2316; Perryman et al. 1996. *Mol. Biochem. Parisitol.* 80:137–147; Reperant et al. 1994. *Vet. Parasitol.* 55: 1–13). However, laboratory studies have shown these immunodominant antigens and other oocyst/sporozoite proteins to be present in other Cryptosporidium species (Nina et al. 1992, supra; Tilley et al. 1990. *Infect. Immun.* 58: 2966–2971); therefore, their presence is not indicative of *C. parvum* infection. This cross-reactivity of immunodominant antigens may explain why commercial antibody-based tests cannot differentiate *C. parvum* from species of Cryptosporidium that are not infectious for humans.

No antibiotics or antiprotozoal drugs licensed for animal use have been approved for prophylaxis or therapy of cryptosporidiosis (Fayer et al. 1997. In *Cryptosporidium and Cryptosporidiosis*, R. Fayer, Ed., CRC Press, New York, N.Y., pages 20 and 30–31). Several researchers have shown, however, that in calves, mice and humans, administration of hyperimmune bovine colostrum, prepared by immunizing cows with extracts of *C. parvum* oocysts, can effectively confer passive immunity against cryptosporidiosis (Fayer et al. 1989. *J. Parasitol.* 75(1):151–153; Fayer et al. 1989. *J. Parasitol.* 75(3):393–397; Fayer et al. 1990. *Infect. Immun.* 58(9):2962–2965; Nord et al. 1990. *AIDS* 4:581–584; Tzipori et al. 1986. *Br. J. Med.* 293:1276–1277; Tzipori et al. 1987. *Lancet* 2:244–245; and Ungar et al. 1990. *Gastroenterology* 98:486–489). Duodenal infusions of hyperimmune bovine colostrum have been reported to ameliorate *C. parvum* infection in AIDS or other immunocompromised patients. Hyperimmune bovine colostrum prepared against oocysts contains neutralizing antibodies that recognize epitopes expressed by all life-cycle stages of Cryptosporidium.

Monoclonal antibodies and immune sera that bind to *C. parvum* sporozoites can neutralize the parasite and either prevent or lessen the severity of infection in animals. The characteristics of many mAbs which specifically react with Cryptosporidium have recently been reviewed; many are neutralizing (Riggs. 1997. In *Cryptosporidium and Cryptosporidiosis*, R. Fayer, Ed., CRC Press, New York, N.Y., Chapter 6). In some instances, the epitope recognized by the monoclonal antibodies has been found in both sporozoites and merozoites. These monoclonal antibodies have been shown to prevent or attenuate infection in studies using animals challenged with *C. parvum*. However, none of these mAb specifically bind exclusively to *C. parvum*. Thus, they cannot be used to specifically identify the presence of *C. parvum* in environmental or patient samples.

Riggs reviews other mAbs reactive with surface membrane antigens and/or apical complex organelles of sporozoites and merozoites; however, no neutralization data are reported (Riggs. 1997, supra). Based on the proteins bound by these mAb and the species involved, these mAb do not selectively identify *C. parvum*-specific proteins.

Although protection against *C. parvum* may be achieved by this type of immunotherapy, the development of resistance to cryptosporidiosis is dependent upon T lymphocytes and secreted lymphokines, in particular, gamma-interferon (Gardner. 1991. *Am. J. Trop. Med. Hyg.* 44(1):49–62; Mead et al. 1991. *J. Infect. Dis.* 163:1297–1304; McDonald et al. 1992. *Infect. Immun.* 60 (8):3325–3331; and Ungar et al. 1991. *J. Immunol.* 147 (3):1014–1022). The humoral response leading to production of protective antibodies specific for *C. parvum* may be dependent upon T cell signaling, but in persons with severe immunodeficiency T cell-mediated immunity is dysfunctional. Passive administration of hyperimmune serum or colostrum that is inhibitory for cryptosporidial parasites may be the only viable alternative for preventing or treating infection in such individuals.

Thus, there is a need for agents useful for the immunotherapy of cryptosporidiosis in both uncompromised and immunocompromised subjects, e.g. AIDS patients, which would prevent or limit the disease. There is also a need for an agent useful for detection of *C. parvum* in environmental samples and for the detection of ongoing *C. parvum* invasion, particularly in its early stages.

SUMMARY OF THE INVENTION

We have identified *C. parvum*-specific antigens. Isolated and recombinant *C. parvum*-specific proteins can be used in a number of different ways. First, the recombinant antigens can be adsorbed to the surface of microtiter plates or to immunoblotting membrane and used in an ELISA format for detection of antibodies in serum of patients exhibiting clinical signs of cryptosporidiosis. Second, the recombinant antigens can be used to prepare monoclonal antibodies (mAb) which selectively identify or which are specific for *C. parvum* oocysts. These mAbs can be used in ELISA and in IFA to detect the parasite in diarrhea or in water samples similar to Cryptosporidium spp.-binding mAb used in commercial diagnostic kits (e.g., Merifluor). Third, the recombinant antigens can be used to generate hyperimmune serum or hyperimmune colostrum or in vaccine development to treat or prevent cryptosporidiosis. Fourth, primers directed to *C. parvum*-specific regions of the DNA sequences can be produced for sensitive detection of the parasite by polymerase chain reaction (PCR), particularly RT-PCR. PCR assays have been developed in a number of laboratories, including our own, to detect less than 10 oocysts in a spiked water sample, but the previously identified primers, as well as primers generated from the nucleotide sequences of SEQ ID NO:1, amplify DNA from all species of Cryptosporidium. However, primers can be used in RT-PCR to specifically identify transcription of *C. parvum*-specific proteins.

We have now discovered a novel recombinant DNA clone designated rCP41 which encodes an oocyst wall protein of *Cryptosporidium parvum*, which may have immunodiagnostic potential for cryptosporidiosis as well as potential for use in the production of hyperimmune colostrum that may be used to confer passive immunity against the parasite. The DNA sequences may be inserted into DNA molecules such as cloning vectors or expression vectors for the transformation of cells and the production of the *C. parvum*-specific proteins.

In accordance with this discovery, it is an object of the invention to provide new proteins and peptides, comprising all or part of the amino acid sequences shown in SEQ ID NO:2, that are specific for C. parvum and that can bind antibodies specific for C. parvum and elicit an immune response specific for C. parvum. This invention, in addition to the above, also encompasses a method of diagnosing Cryptosporidium infection of a subject, comprising: contacting a body fluid obtained from the subject with the peptide of this invention; and detecting any selective binding of the peptide to any anti-Cryptosporidium antibodies in the body fluid.

It is also an object of the invention to provide new proteins and peptides that are specific for C. parvum and that can therefore be used to generate antibodies for identifying the presence of C. parvum in biological samples and in water. It is part of this invention to provide the genes which encode these peptides.

In particular, this invention comprises a method of diagnosing Cryptosporidium infection of a subject, comprising: contacting a body substance obtained from the subject with an anti-C. parvum antibody; and detecting any selective binding of the antibody to any antigenic C. parvum-specific peptide present in the body substance.

Further, as a public health issue, there is a need for a method to identify and enumerate the presence of Cryptosporidium parvum in water. This invention comprises a method of identifying the presence of C. parvum in water, comprising: contacting a sample from the water source, or a concentrate of a sample from the water source, with an anti-C. parvum antibody; and detecting any selective binding of the antibody to any antigenic C. parvum-specific peptide present in the water.

It is also an object of the invention to provide new proteins and peptides that are specific for C. parvum and that can therefore be used to generate monoclonal or polyclonal antibodies, hyperimmune serum, or hyperimmune colostrum for use in immuno-therapeutic methods for preventing and treating C. parvum infection. It is part of this invention to provide the genes which encode these peptides.

Another object of the invention relates to a method of inhibiting or ameliorating a Cryptosporidium infection in an individual comprising administering to an individual in need of such treatment an amount of an anti-CP41 or anti-rCP41 antibody or hyperimmune colostrum or hyperimmune sera effective to prevent or decrease the severity of cryptosporidiosis.

It is an additional object of this invention to provide new proteins and peptides, and the genes which encode them, that are effective for the immunization of animals against cryptosporidiosis.

An added object of the invention is to provide compositions and methods useful for protecting animals against cryptosporidiosis.

Another object of the invention relates to a method of protecting an individual comprising administering to an individual an amount of proteins and peptides of this invention capable of eliciting from the individual a B- or T-cell immune response effective to prevent or to decrease the severity of cryptosporidiosis.

Further, the invention can comprise fusion proteins comprising one of the peptides described above comprising one or more epitopes of rCP41 protein wherein said rCP41 protein comprises an amino acid sequence shown in SEQ ID NO:2 and wherein said protein is antigenic and effective to elicit an immune response against Cryptosporidium parvum in a host animal and a second unrelated peptide expressed by a regulatory DNA segment operably coupled to the DNA segment described above that encodes the peptide of this invention. In addition, the invention can comprise fusion proteins comprising the unrelated peptide expressed by a regulatory DNA segment operably coupled to a DNA nucleotide sequence encoding a fusion protein comprising one of the peptides described above comprising one or more epitopes of rCP41 protein wherein said rCP41 protein comprises an amino acid sequence shown in SEQ ID NO:2 and wherein said protein is antigenic and effective to elicit an immune response against Cryptosporidium parvum in a host animal operably coupled to yet another unrelated polypeptide sequence (different from the regulatory protein). It is part of this invention to provide the genes which encode these fusion proteins. Still part of this invention are fusion RNA and DNA polymers comprising the RNA or DNA of this invention and a second unrelated polyRNA or polyDNA segment.

Additionally, it is an object of the invention to provide DNA primers from the sequence described in SEQ ID NO:1. The invention further comprises a method for specifically identifying C. parvum which comprises amplifying a subject mRNA by the RT-PCR method with the use of the above-mentioned DNA primers and thus assaying the expression of the CP41 gene.

Also part of this invention is a Cryptosporidium diagnostic kit, comprising anti-Cryptosporidium-specific antibodies; and instructions for the use of the kit.

Furthermore, this invention also provides a Cryptosporidium diagnostic kit, comprising the proteins and peptides of this invention; and instructions for use of the kit.

Other objects and advantages of this invention will become readily apparent from the ensuing description.

BRIEF DESCRIPTION OF THE DRAWINGS

FIG. 2 shows the DNA sequence and the predicted amino acid sequence of CP41 DNA clone isolated from Cryptosporidium parvum oocysts. Putative ATG start sites are indicated in bold.

DETAILED DESCRIPTION OF THE INVENTION

Figure 1:
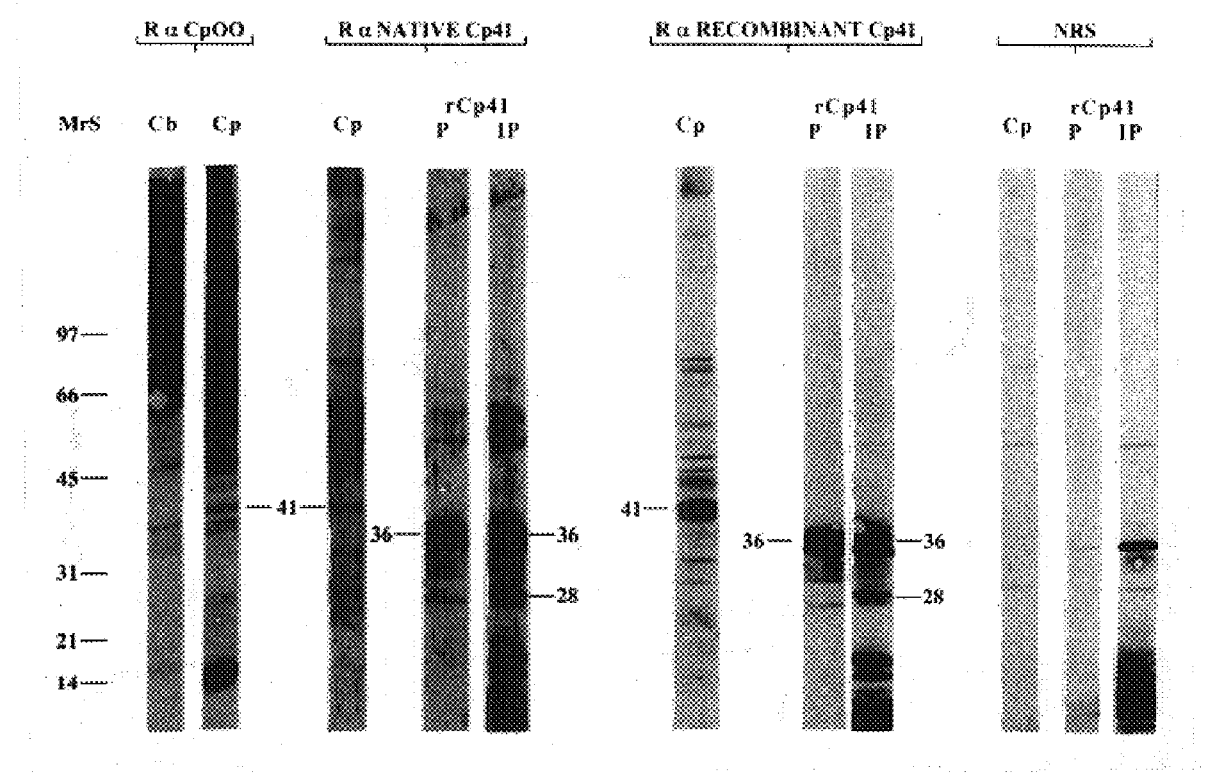
FIG. 1 shows the immunostaining of SDS-PAGE fractionated native Cryptosporidium parvum (Cp) or C. baileyi (Cb) oocyst protein, or NiNTA-purified (P) and unpurified (IP) recombinant CP41 protein (rCp41) with rabbit sera to whole C. parvum oocyst protein (R α CpOO), native (R α NATIVE Cp41) or recombinant (R α RECOMBINANT Cp41) Cp41 antigen, or normal control rabbit sera (NRS). MrS, molecular weight standards.

The present invention provides an isolated 41 kDa protein, CP41, and rCP41, the recombinant 36 kDa and 28 kDa proteins, all of which are specific for *Cryptosporidium parvum* and the nucleic acid sequences that encode these proteins. Antibodies resulting from immunizations with the recombinant 36 and 28 kDa proteins specifically bind the native 41 kDa protein, CP41, which is specific for *C. parvum*. Antibodies resulting from immunizations with the native 41 kDa protein specifically bind rCP41, the recombinant 36 and 28 kDa proteins, which are specific for *C. parvum*. The invention encompasses a recombinant bacteriophage clone, designated rCP41 (GenBank, Accession No. AF144621) comprising a nucleotide sequence (SEQ ID No. 1) encoding rCP41 recombinant proteins. The predicted amino acid sequence (SEQ ID NO:2) of rCP41 (i.e., the 36 and 28 kDa proteins) is shown in FIG. 2. The invention encompasses DNA sequences which encode peptides having amino acid sequences that are homologous to that of FIG. 2. "Homologous" peptides are defined herein as peptides having an amino acid sequence sufficiently duplicative of CP41 protein or rCP41 proteins to be antigenic and capable of eliciting antibody which specifically and selectively bind to *C. parvum*. DNA sequences encoding CP41 protein and rCP41 proteins with the amino acid sequence (SEQ ID NO:2) shown in FIG. 2 and DNA sequences which encode homologous proteins and which also hybridize to the DNA sequence of FIG. 2 (or its complement) under stringent conditions are particularly preferred.

Further, because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention. DNA sequences which are substantially homologous to the nucleotide sequence of FIG. 2 are also encompassed by the invention. As defined herein, two DNA sequences are substantially homologous when at least 85% (preferably at least 90% and most preferably 95%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al. 1989. Molecular Cloning: A Laboratory Manual, Cold Spring Harbor Laboratory, Cold Spring, N.Y., or DNA Cloning: A Practical Approach, Vol. I and II (Ed. D. N. Glover), IRL Press, Oxford, 1985. Sambrook et al. describe highly stringent conditions as a hybridization temperature 5–10° C. below the $T_m$ of a perfectly matched target and probe; thus, sequences that are "substantially homologous" would hybridize under such conditions.

The present invention also encompasses CP41 variants. A preferred CP41 variant is one having at least 80% amino acid sequence similarity to the CP41 amino acid sequence (SEQ ID NO:2), a more preferred CP41 variant is one having at least 90% amino acid sequence similarity to SEQ ID NO:2 and a most preferred CP41 variant is one having at least 95% amino acid sequence similarity to SEQ ID NO:2 as defined by the algorithm, CLUSTRAL or PILEUP.

A "variant" of CP41 may have an amino acid sequence that is different by one or more amino acid "substitutions". The variant may have "conservative substitutions", wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software. The term "biological activity" refers to rCP41 having structural, regulatory or biochemical functions of the naturally occurring CP41. Likewise, "immunological activity" defines the capability of the natural, recombinant or synthetic CP41, or any oligopeptide thereof, to induce a specific immune response in appropriate animals or cells and to bind with specific antibodies.

The phrase "conservative substitution" also includes the use of a chemically derivatized residue in place of a non-derivatized residue. "Chemical derivative" refers to the chemical modification of a nucleic acid sequence encoding CP41 or the encoded CP41 wherein the subject nucleic acid or polypeptide has one or more residues chemically derivatized by reaction of a functional side group. Examples of such modifications would be replacement of hydrogen by an alkyl, acyl, or amino group; however, replacements are not limited to these groups. A nucleic acid derivative would encode a polypeptide which retains essential biological characteristics of natural CP41. Also included are those peptides which contain one or more naturally-occurring amino acid derivatives of the twenty standard amino acids, e.g., 5-hydroxylysine or ornithine may be substituted for lysine.

The term "peptide" as used herein refers to a molecular chain of amino acids with a biological activity (e.g., capable of binding antibody specific for *C. parvum*), and does not refer to a specific length of the product. Thus, inter alia, proteins, oligopeptides, polypeptides and fusion proteins as well as fusion peptides are included. Further, CP41 and rCP41 are interchangeable as reagents for detecting *C. parvum*-specific antibodies, for generating *C. parvum*-specific antibodies, and for vaccine development. Thus, inter alia, reference to CP41 encompasses rCP41, and reference to rCP41 encompasses CP41.

The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, humanized, CDR-grafted, and single chain antibodies, and the like. Fragments of immunoglobulins, including Fab fragments and fragments produced by an expression library, including phage display. See, e.g., Paul, Fundamental Immunology, Third Ed., 1993, Raven Press, New York, for antibody structure and terminology.

The phrases "specifically binds to" or "specifically immunoreactive with", when referring to an antibody or other binding moiety refers to a binding reaction which is determinative of the presence of the target analyte in the presence of a heterogeneous population of proteins and other biologics. Thus, under designated assay conditions, the specified binding moieties bind preferentially to a particular target analyte and do not bind in a significant amount to other components present in a test sample. Specific binding to a target analyte under such conditions may require a binding moiety that is selected for its specificity for a particular target analyte. A variety of immunoassay formats may be used to select antibodies specifically immunoreactive with a particular protein. For example, solid-phase ELISA immunoassays are routinely used to select monoclonal antibodies specifically immunoreactive with an analyte. See Harlow and Lane (1988) Antibodies, A Laboratory Manual, Cold Spring Harbor Publications, New York, for a description of immunoassay formats and conditions that can be used to determine specific immuno- reactivity. Typically a specific or selective reaction will be at least twice background signal to noise and more typically more than 10 to 100 times background.

The DNA sequences of the invention can be used to prepare recombinant DNA molecules by cloning in any suitable vector. A variety of vector-host combinations may be employed in practicing the present invention. Host cells may be either prokaryotic or eukaryotic, and, when the host cells are bacterial cells, they may be either gram-negative or gram-positive bacteria. Without being limited thereto, examples of hosts suitable for use herein are prokaryotic and eukaryotic hosts such as *E. coli* K12 and related bacteria, *Saccharomyces cerevisiae*, Sf9 or Sf21 insect cells (*Spodoptera frugiperda*), Chinese hamster ovary cells, and plant cells in culture. However, other hosts may also be utilized.

Vectors used in practicing the present invention are selected to be operable as cloning vectors or expression vectors in the selected host cell. Numerous vectors are known to those of skill in the art, and selection of an appropriate vector and host cell is a matter of choice. This invention encompasses a hybrid vector, that comprises a vector capable of replication, transcription and expression of DNA segments operably coupled thereto; and a DNA segment encoding a polypeptide of this invention comprising the peptide disclosed herein operatively coupled thereto, wherein when the vector is placed in an appropriate host it can express the polypeptide encoded by the DNA segment. Examples of such vectors are pGex (Pharmacia), baculovirus, pET-9d (Novagen) or pRSET T7 (Invitrogen). However, other vectors may also be utilized. The vector may be a eukaryotic or a prokaryotic vector depending on the host selected for transfection and in which the gene product is going to be expressed. Still part of this invention is another hybrid vector, that comprises a vector capable of replication, transcription and expression of DNA segments operably coupled thereto; and a DNA segment comprising a DNA fragment encoding at least one of the polypeptides of the invention and a second unrelated DNA segment, both sequences being operably coupled to one another and to the vector. The preparation of the hybrid vector described above is known in the art and need not be further described herein (Smith, D., and Johnson, K., "Single Step Purification of Polypeptides Expressed in *E. Coli* as Fusions with Glutathione S-transferase", Gene 67:31(1988); Studier, F. W., Rosenberg, A. H., Dunn, J. J., and Dubendorff, J. W., "Use of T7 RNA Polymerase to Direct Expression of Cloned Genes", Meth. Enzymol. 185:60–89(1990)). The vectors may, for example, be bacteriophage, plasmids, viruses, or hybrids thereof. A number of prokaryotic expression vectors are described in U.S. Pat. Nos. 4,652,525, 4,440,859, 4,436,815, and 4,342,832, and a number of eukaryotic expression vectors have also been described in U.S. Pat. Nos. 4,546,082, 4,510,245, and 4,446,235. Further, the vectors may be non-fusion vectors (i.e., those producing the antigenic protein of the invention not fused to any heterologous polypeptide), or alternatively, fusion vector (i.e., those producing the antigenic protein fused to a vector encoded polypeptide). The fusion proteins would of course vary with the particular vector chosen. Suitable non-fusion plasmid vectors for use with *E. coli* include but are not limited to pTrc99 for use with *E. coli* JM 105, or pANK-12, pANH-1 or pPL2 for use with *E. coli* MZ 1. Conversely, suitable fusion plasmid vectors include pGEX and pMC1871 for use with *E. coli* JM 105, pMAL with *E. coli* PR 722, pVB2 with *E. coli* LA5709, pTrcHis with *E. coli* INV F' and DH5, pCO5 with *E. coli* N6405, and pRIT2T or pEZZ 18 with *E. coli* N4830-1. Other, non-*E. coli* expression systems which may also be employed include pAc360 or pBluescript for use with SP2 or High 5 insect cells, pYesHis with the yeast *C. cerevisiae* INVSc1 or INVSc2, pLS405 with *Salmonella dublin* SL598, and pYUB12 with *Mycobacterium smegmatis* or *M. bovis*. Still other suitable vector-host combinations that may be used in practicing the instant invention are described, for example, in U.S. Pat. No. 5,122,471, the contents of which are incorporated by reference herein.

Within each specific vector, various sites may be selected for insertion of the isolated DNA sequence. These sites are usually designated by the restriction enzyme or endonuclease that cuts them. For example, in pBR322, the Pst I site is located in the gene for penicillinase between the nucleotide triplets that code for amino acids 181 and 182 of the penicillinase protein.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences of the invention may be inserted into the desired vector by known techniques. If, however, the vector is to serve as an expression vector, the vector should have a promoter, and the DNA sequence should be inserted in the vector downstream of the promoter and operationally associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be.

The antigenic peptides of the invention are produced by growing host cells transformed by the expression vectors described above under conditions whereby the antigen is produced. The antigens are then isolated from the host cells. The selection of the appropriate growth conditions and recovery methods are well within the skill of the art. A recombinant CP41 protein has been produced in the pTrcHis expression system. The recombinant CP41 antigen is produced as two related proteins; a 36 kDa protein and a 28 kDa protein have been identified.

Labeled oligonucleotide probes may be readily prepared using techniques known in the art, such as automated synthesis, using the nucleotide sequence encoding rCP41 disclosed herein. The particular nucleotide sequences selected are chosen so as to correspond to codons encoding an amino acid sequence of the antigen. While the exact length of the probe is not critical, it is generally recognized that probes from about 15 to about 20 base pairs are usually effective. Greater selectivity may be achieved using longer probes. The probes may be labeled with a marker, such as a radionucleotide or biotin using standard procedures, and used to screen the libraries by Southern hybridization. Procedures for the hybridization assay are described, for example, in U.S. Pat. No. 5,041,378, and in Nucleic Acid Hybridization, (Ed. Hames and Higgins) 1985, the contents of each of which are incorporated by reference herein. Once a clone from the screened library has been identified by positive hybridization, it can be confirmed by methods such as restriction enzyme analysis and DNA sequencing that the clone contains a gene that encodes the amino acid sequence comprising all or part of SEQ ID NO:2 or a homologous amino acid sequence.

With C. parvum, results indicate (See Example 13) that CP41 primers will probably not be useful for a species-specific PCR test based on genomic DNA, but that the CP41 primers are useful for species-specific RT-PCR analysis of total Cryptosporidium RNA (Example 14).

For RT-PCR, mRNA is transcribed into cDNA using a gene specific primer (or oligo dT if the gene sequence is unknown) and reverse transcriptase. After the first strand cDNA is produced (the RT reaction), the second DNA strand is generated using an upstream gene specific primer. This second reaction, i.e., the PCR part, with downstream and upstream primers is repeated 25–35 times to produce a DNA fragment originating from the mRNA (See Example 14).

The peptides and proteins of this invention can be used as immunogens to generate antibodies that are selectively specific for C. parvum. Thus, CP41 and rCP41 can be used to generate monoclonal and polyclonal antibodies and hyperimmune serum and hyperimmune colostrum. To prepare antibodies, a host animal is immunized using the CP41 protein as the immunogen. The host serum or plasma is collected following an appropriate time interval to provide a composition comprising antibodies reactive with the immunogen. Methods of antibody (polyclonal and monoclonal) production and isolation are well known in the art. See, for example, Harlow et al. 1988, supra. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-antibody.

In another embodiment, the monoclonal antibody of the invention is a chimeric monoclonal antibody or a humanized monoclonal antibody, produced by techniques well-known in the art.

The peptides and proteins of this invention can be used as immunogens in vaccines for vaccination against C. parvum. The vaccines can be used to prevent or reduce susceptibility to disease caused by C. parvum. While the peptides are effective for eliciting antibody production in a variety of animals, the peptides are particularly preferred for the treatment of bovine animals.

The peptides and proteins of this invention can be formulated as univalent and multivalent vaccines. The CP41 peptide can be used as produced or isolated by the methods described above. The protein can be mixed, conjugated or fused with other antigens, including B or T cell epitopes of other antigens. In addition to its utility as a primary immunogen, the CP41 peptide can be used as a carrier protein to confer or enhance immunogenicity of other antigens.

When a haptenic peptide of protein CP41 is used, (i.e., a peptide which reacts with anti-CP41 specific antibodies, but cannot itself elicit an immune response), it can be conjugated to an immunogenic carrier molecule. For example, an oligopeptide containing one or more epitopes of CP41 protein may be haptenic. Conjugation to an immunogenic carrier can render the oligopeptide immunogenic. Preferred carrier proteins for the haptenic peptides of CP41 are tetanus toxin or toxoid, diphtheria toxin or toxoid and any mutant forms of these proteins such as $CRM_{197}$. Others include exotoxin A of Pseudomonas, heat labile toxin of E. coli and rotaviral particles (including rotavirus and VP6 particles). Alternatively, a fragment or epitope of the carrier protein or other immunogenic protein can be used. For example, the hapten can be coupled to a T cell epitope of a bacterial toxin. See U.S. Pat. Nos. 5,785,973 and 5,601,831, the teachings of which are incorporated herein. In addition, immunogenicity of CP41 could be increased by conjugation of a carrier molecule, for example, dipalmityl lysine. (See Hopp, 1984. Mol. Immunol. 21: 13–16, incorporated herein by reference.)

The peptides or proteins of this invention in monomeric or multimeric form can be incorporated into vaccines capable of inducing protective immunity against oocysts/sporozoites of C. parvum. The peptides or proteins of this invention can be administered as multivalent subunit vaccines in combination with other antigens of C. parvum. For example, they may be administered in conjunction with other oocyst/sporozoite components of C. parvum. Furthermore, it will be understood that peptides specific for a plurality of C. parvum stages and Cryptosporidium species may be incorporated in the same vaccine composition to provide a multivalent vaccine. In addition, the vaccine composition may comprise antigens to provide immunity against other diseases in addition to cryptosporidiosis.

The conjugates can be formed by standard techniques for coupling proteinaceous materials. Fusions can be expressed from fused gene constructs prepared by recombinant DNA techniques as described. Also provided herein is a fusion protein that comprises the polypeptide of the invention in all its different antigenic forms and a second unrelated polypeptide encoded by, e.g., a DNA segment operably coupled to the DNA segment encoding the polypeptide of the invention. An example of the second unrelated polypeptide is beta-galactosidase, where the DNA segment encoding this gene product also contains regulatory sequences. However, other polypeptides may also be used, such as to provide a large protein component to increase immunogenicity. If the gene encoding the polypeptide of the invention is cloned within the beta-galactosidase gene, the two polypeptides may be expressed as a fusion protein and the amount of fusion protein produced is controlled by the regulatory sequences of the beta-galactosidase gene.

The preparation of vaccines which contain peptide sequences as active ingredients is generally well understood in the art, as exemplified by U.S. Pat. Nos.: 4,474,757; 4,493,795; 4,608,251; 4,601,903; 4,599,231; and 4,599,230, all incorporated herein by reference. In formulating the vaccine compositions with the peptide or protein, alone or in the various combinations described, the immunogen is adjusted to an appropriate concentration and formulated with any suitable vaccine adjuvant and/or vaccine stabilizer. Typical stabilizers are, for example, sucrose, an alkali metal hydrogen phosphate salt, glutamate, serum albumin, gelatin, or casein. The stabilizer may be any one or more of the foregoing. Suitable adjuvants include, but are not limited to: surface active substances, e.g., hexadecylamine, octadecylamine, octadecyl amino acid esters, lysolecithin, dimethyl-dioctadecylammonium bromide, methoxyhexadecylglycerol, and pluronic polyols; polyamines, e.g., pyran, dextran-sulfate, poly IC, carbopol; peptides, e.g., muramyl dipeptide, dimethylglycine, tuftsin; oil emulsions; and mineral gels, e.g., aluminum hydroxide, aluminum phosphate, etc. and immune stimulating complexes. The adjuvant may be, for example, alum or a composition containing a vegetable oil, isomannide monooleate and aluminum mono-stearate. The immunogen may also be incorporated into liposomes, or conjugated to polysaccharides and/or other polymers for use in a vaccine formulation.

Also part of this invention is a composition that comprises the peptide of this invention; and a carrier, preferably a biologically-acceptable carrier, and more preferably a pharmaceutically-acceptable carrier. Typical carriers are aqueous carriers such as water, buffered aqueous solutions, aqueous alcoholic mixtures, and the like. Compositions comprising carriers that are for pharmaceutical use, particularly for use in humans, comprise a carrier that is pharmaceutically-acceptable. Examples of such carriers are known in the art and need therefore not be provided herein.

Typically, such vaccines are prepared as injectables: either as liquid solutions or suspensions, solid forms suitable for solution in, or suspension in, liquid prior to injection may also be prepared. The CP41 protein preparation could also be emulsified. The peptides may be administered to a human or target animal by any convenient route, such as subcutaneously, intraperitoneally, intramuscularly, intradermally, intravenously, orally, intranasally, or preferably intramammarily, in the presence of a physiologically acceptable diluent. The antigens may be administered in a single dose or in a plurality of doses. The antigens of the present invention may be stored under refrigeration or in frozen or lyophilized form. The proteins are administered to the target animal in an amount effective to elicit a protective immune response against *C. parvum*, as compared to a control. The effective amount will vary with the particular target animal, its age and size, and may be readily determined by the practitioner skilled in the art. Suitable regimes for initial administration and booster shots will also be variable, but may be typified by an initial administration followed by subsequent inoculations or other administrations.

The antigenic peptides of the present invention were used to immunize animals against *C. parvum*. While the peptides are effective for eliciting antibody production in a variety of animals, the peptides are particularly preferred for the treatment of bovine animals. In accordance with the preferred embodiment, the proteins are used to immunize bovine animals for the production of hyperimmune colostrum containing antibodies to *C. parvum*. The hyperimmune colostrum so produced may be administered to target animals, particularly young or immunodeficient animals, to confer passive immunity against cryptosporidiosis. Without being limited thereto, the hyper-immune colostrum is particularly beneficial for the treatment of humans and bovine animals. Techniques for the production of hyperimmune colostrum and its use are known in the art and are described in, for example Fayer et al., Nord et al., Tzipori et al., Ungar et al., referred to above. In addition, the method used by Jenkins et al. to successfully obtain high levels of colostral anti-Cryptosporidium antibodies is described in U.S. Pat. No. 5,591,434, the contents of which are herein incorporated by reference. Briefly, purified recombinant CP41 is emulsified 1:1 in Freund's Incomplete Adjuvant and used to immunize separate cows by intramuscular injection 8 weeks before parturition. The cows receive intramammary injections of a similar antigen preparation at 6 and 4 weeks before parturition. The primary immunization consists of 0.25 mg recombinant CP41 protein (or an equivalent amount of control protein). The second and third immunizations consist of 0.25 mg protein injected into the left front and left rear quarters and 0.1 mg protein injected into the right front and right rear quarters. After parturition, the cows are milked twice daily for 3 days and colostrum is prepared using standard procedures. The antibody response to recombinant CP41 and control antigen is assessed by ELISA as described below in Example 15. Cows immunized with recombinant CP41 antigen would be expected to exhibit high colostral immunoglobulin titers against native and recombinant CP41, e.g., between $10^4$ and $10^5$ at the first milking. This brief description of the method is set forth to illustrate the general procedure and is not intended to limit the scope of the invention.

While the protein may be administered to the target animal directly, it is also envisioned that the recombinant DNA containing an amino acid sequence encoding the protein could be administered to the animal as the immunizing agent. Suitable techniques for the treatment of animals with recombinant DNA are described, for example, by Tang et al., Nature 356:152–154 (1992), and Ulmer et al., Science 259:1745–1749 (1993), the contents of each of which are incorporated by reference herein.

Also provided herein is a biologically pure DNA segment encoding the polypeptide of the invention. In addition, provided herein are the DNA sequences for both strands of each clone. Moreover, given the degeneracy of the genetic code, there may be multiple DNA sequences encoding the same polypeptide. All are part of this invention.

The immunotherapy of cryptosporidiosis in humans and animals may be conducted by the oral (intraluminal gastrointestinal) administration of the antibodies of the invention to patients with cryptosporidiosis to effectively reduce their symptomatology.

Also an important part of this invention is a method of diagnosing Cryptosporidium infection, that comprises contacting a body substance with an anti-Cryptosporidium antibody having specificity for the polypeptide of this invention; and detecting any selective binding of the antibody to any antigenic Cryptosporidium peptides present in the body substance. The anti-Cryptosporidium antibodies may be monoclonal or polyclonal. Also provided herein is a method of detecting the presence of *Cryptosporidium parvum* in water samples. The detection of the antibody-polypeptide complex may be conducted by any method known in the art. This includes solid phase, double antibody, sandwich double antibody, and triple antibody assays, and the like, including radioimmunoassay, enzyme-linked immunosorbent assay, fluorescent assay, including flow cytometry, chemiluminescent assay, competitive immunoassay, membrane-based immunoassay, immunomagnetic separation, precipitation, agglutination, antigen capture, or the like.

For example, flow cytometric analysis can be used to detect C. parvum in stool samples and in water samples. Flow cytometry is relatively rapid and easily incorporated into routine clinical hospital laboratories equipped with a flow cytometer to screen samples. Such a procedure has been described by Arrowood et al. 1995. J. Parasitol. 81 (3): 404–409 and is herein incorporated by reference. Briefly, fecal samples are collected from bovine or human individuals, diluted in 2.5% potassium dichromate, and homogenized by vortexing. Aliquots (200 μl) of the vortexed samples are centrifuged over microscale discontinuous sucrose gradients. The fractions are collected, washed, and incubated with a FITC-labeled C. parvum-specific mAb for 30 min at 37° C. For positive controls: fecal samples are collected from control (uninfected) bovine or human individuals, suspended in 2.5% potassium dichromate, and homogenized by vortexing. Purified oocytes are added to these (previously uninfected) samples at concentrations of $10^5$, $10^4$, $10^3$, and $10^2$ per ml. These control samples are centrifuged over microscale discontinuous sucrose gradients, washed, and stained as above. Volumes of samples and controls are adjusted to 600 μl with phosphate-buffered saline (PBS) and are assayed by using logical gating of forward/side scatter and fluorescence signal on a flow cytometer. Positive control seeded samples have shown a linear correlation with the number of oocysts recovered from the gradients (Arrowood et al. 1995, supra). Flow cytometric analysis of stool samples from infected bovine and human individuals would be expected to be at least 10 times more sensitive than conventional immunofluorescent assays. The preceding example is set forth to illustrate the general methodology and is not intended to limit the scope of the invention. Thus, the procedure can encompass different quantities, reagents, and steps. Flow cytometric methodology is well known to one of skill in the art.

Water samples can be tested for the presence of even very low numbers of C. parvum, by combining magnetic separation methods, e.g., MACS, with flow cytometric methods to enrich or concentrate the low numbers of C. parvum in the sample. For example, C. parvum can be concentrated using biotin-labeled anti-Cryptosporidium-specific mAbs, together with anti-biotin-labeled magnetic beads. Because of the microscopic size of the MAC beads, any oocysts positively selected by this method can then be stained with FITC-anti-rCP41 mAb, specific for C. parvum, and rapidly and specifically identified by flow cytometric analysis.

In a most preferred embodiment of the presently claimed diagnostic methods for identifying presence of C. parvum oocysts, the method comprises the steps of: collecting a water sample; isolating an oocyst-rich fraction from the water sample by concentration with immunomagnetic methodology; staining the concentrated oocysts with *C. parvum*-specific mAb, and determining the actual number, if any, of *C. parvum* oocysts.

Additionally provided herein is a method of diagnosing Cryptosporidium infection, that comprises contacting a body substance with one of the polypeptides of this invention; and detecting any selective binding of the polypeptide to any anti-Cryptosporidium antibodies in the body substance. As in the previous case, the present antibody-polypeptide binding complex may be detected by a variety of methods such as those listed above. Examples of body substances are stools and other liquid or solid body output or tissue samples obtained from a subject. Examples of body fluids are blood, serum, saliva, urine, and the like. Methods for the preparation of the body substance and the body fluid are standard in the art and need not be further detailed herein (see, for example, Manual of Clinical Microbiology, Chapter 8, "Collection, Handling and Processing of Specimens", 4th edition, Eds, Lennette, E. H., Balows, A., Hausler, W. J. and Shadorny, A. J., American Society for Microbiology (1986)).

Still part of this invention is a kit for the diagnosis of Cryptosporidium infection, that comprises the peptide(s) of this invention; and instructions for use of the kit. This kit may be utilized for the detection of endogenous antibodies produced by a subject that is afflicted with cryptosporidiosis. Even at the early stages where the parasite is commencing invasion of a subject's cells, some amount of Cryptosporidium specific antibody may be detected in serum.

Also provided herein is another Cryptosporidium diagnostic kit, that comprises anti-Cryptosporidium antibodies having specificity for one of the polypeptides of this invention; and instructions for use of the kit. Thus, kit may be utilized for the detection of Cryptosporidium peptides, a sign that there is parasite present in the subject being tested.

In addition to the above, the kits may also comprise a control, anti-antibodies, protein A/G, and the like, suitable for conducting the different assays referred to above.

EXAMPLES

Having now generally described this invention, the same will be better understood by reference to certain specific examples, which are included herein only to further illustrate the invention and are not intended to limit the scope of the invention as defined by the claims.

EXAMPLE 1

Preparation of Parasites

*Cryptosporidium parvum* (AUCP-1) strain oocysts were obtained by infecting a 1 day old calf with $10^6$ oocysts. The calf was obtained at birth from the dairy herd at the Beltsville Agricultural Research Center and housed in a 4×6 m concrete-floored pen with cinder block walls in a sanitized masonry building. Feces were collected from days 3–10 post-infection, pooled, and passed through a series of sieves of increasingly finer mesh, ending with a No. 325 mesh screen. Sieved fecal material was mixed with 2M sucrose and subjected to continuous flow centrifugation followed by purification over a cesium chloride gradient using the procedures described by Kilani et al. 1987. *Am. J. Trop. Med. Hyg.* 36: 505–508) for purification of *C. parvum* oocysts. Clean oocysts were resuspended in distilled water, stored at 4° C., and used from 1–6 months after collection, depending on objectives of the experiment. Limited numbers of oocysts of other Cryptosporidium species were obtained from outside sources: *C. baileyi* (B. Blagburn, Auburn University), *C. meleagridis* (M. Levy, North Carolina State University), *C. serpentis* (T. Graczyk, Johns Hopkins University), and *C. wrairi* (C. E. Chrisp, University of Michigan, Ann Arbor).

EXAMPLE 2

Preparation of Parasite Nucleic Acid and Protein

Cryptosporidium oocysts destined for RNA and DNA extraction were treated for 30 min. with 2.5% sodium hypochlorite (50% Clorox), washed 5 times with deionized $H_2O$, resuspended in 1.0 ml $dH_2O$, and immersed drop-wise into a mortar containing liquid nitrogen. The frozen parasites were ground in liquid nitrogen to a fine powder which was transferred to a tube containing either RNA or DNA extraction buffer. Total C. parvum RNA was isolated in TRIZOL reagent following manufacturers directions (Gibco-BRL, Gaithersburg, Md.). A high salt concentration step was incorporated as per instructions from the manufacturer to remove polysaccharide which appears to exist in large quantities in Cryptosporidium. DNA of C. parvum was prepared by treating the parasite extract with 1% sodium dodecylsulfate (SDS) and 50 µg/ml proteinase K (Gibco/BRL, Gaithersburg, Md.) as described (Jenkins et al. 1993. Infect. Immun. 61: 2377–2382). RNA and DNA yields were estimated by $O.D._{260}/O.D._{280}$ reading. Total oocyst protein was prepared by resuspending the parasites in protein extraction buffer (10 mM Tris-HCl pH 7.3, 1 mM $MgCl_2$) in the presence of phenylmethylsulfonyl-fluoride (PMSF). The oocysts were subjected to five freeze-thaw cycles between dry ice-EtOH and 37° C. water baths.

EXAMPLE 3

SDS-PAGE/immunoblotting of Native and Recombinant C. parvum Protein

Protein extracts of Cryptosporidium oocysts were treated with sample buffer containing 2-mercaptoethanol, heated for 3 min. in a boiling water bath, fractionated by 7.5–15% gradient SDS-PAGE, and transblotted to Immobilon (Millipore, Bedford, Mass.) membrane as described (Jenkins et al. 1993, supra). The antigen-impregnated membranes were treated briefly with phosphate-buffered saline (PBS), then immersed in PBS containing 2% non-fat dry milk (NFDM) to block non-specific antibody binding in subsequent steps. After blocking, the membranes were incubated for 2 hr with a 1:100 dilution of rabbit antisera to native or recombinant C. parvum antigen in PBS containing 0.05% Tween 20 (PBS-Tw20). The membranes were then probed for 2 hr with biotinylated goat-anti-rabbit IgG (H+L chain sp., Vector Laboratories, Burlingame, Calif.) followed by a 1 hr incubation with avidin-peroxidase (Sigma Chemical Co., St. Louis, Mo.), and final treatment with peroxidase substrate (0.5 mg/ml 4-chloro-1-napthol, 0.015% $H_2O_2$ in PBS) to visualize antibody binding. The membranes were washed three times between each incubation step with PBS-Tw20.

EXAMPLE 4

Identification of Cryptosporidium parvum-specific 41 kDa Protein

Total oocyst protein extracted from C. parvum, C. baileyi, C. meleagridis, and C. serpentis was electrophoresed in adjacent lanes of a 7.5%–15% gradient SDS-PAGE ($10^7$ oocysts/lane) and transblotted to nitrocellulose membrane (Schleicher and Schuell, Keene, N.H.). The blots were immunostained with rabbit antisera raised against total C. parvum oocyst protein to identify antigens unique to C. parvum.

Antisera raised against total C. parvum oocyst protein recognized a number of antigens of C. parvum and C. baileyi (FIG. 1). A similar recognition pattern was observed with C. meleagridis and C. serpentis (data not shown). Although the majority of antigens were common to all Cryptosporidium species, a few antigens were unique to C. parvum. In particular, a 41 kDa protein was present in C. parvum but not in the other Cryptosporidium species (FIG. 1).

EXAMPLE 5

Preparation of Antisera to Cryptosporidium parvum 41 kDa Protein

A section of nitrocellulose adjacent to the unique p41 antigen in an unlabeled section of the blot was excised, ground in a mini-mortar and pestle, resuspended in PBS containing ImmunoMax SR adjuvant (Zonagen, The Woodlands, Tex.), and used to immunize New Zealand White rabbits (Covance, Denver, Pa.) by intramuscular injection. The rabbits received subsequent booster immunization 4 wks after the primary immunization and were then bled for serum by central auricular artery puncture two weeks after the last booster immunization to obtain monospecific antisera to the p41 protein.

EXAMPLE 6

Immunoscreening Cryptosporidium parvum Genomic DNA Libraries for p41 Clones

Genomic C. parvum DNA was subjected to partial digestion with Tsp5901 restriction enzyme (recognition site –AATT, New England BioLabs, Beverly, Mass.) to obtain fragments approximately 1 kb in length. The DNA fragments were cloned into the EcoRI site of lambda Zap II bacteriophage expression system (Stratagene, La Jolla, Calif.). Bacteriophage containing C. parvum genomic DNA were screened at a density of $10^4$ plaques per petri dish using directions supplied by the manufacturer (Stratagene). Nitrocellulose filters soaked in 10 mM isopropylthiogalactopyranoside (IPTG) were overlaid onto the petri dishes containing phage plaques for 4 h at 37° C. The filters were washed with PBS, treated with PBS-NFDM, and then probed with rabbit antisera to native Cp41 protein. Antibody binding was visualized as described above for immunoblotting. Positive phage were picked and subjected to multiple rounds of screening until a clonal population was obtained. A recombinant bacteriophage clone encoding epitopes of the C. parvum 41 kDa antigen was designated rCP41 (GenBank, Accession No. AF144621).

EXAMPLE 7

DNA Sequencing of C. parvum cDNA

Recombinant pBLUESCRIPT plasmid DNA was excised from recombinant lambda Zap bacteriophage using an excision protocol supplied by the manufacturer (Stratagene). The DNA sequence of the recombinant pBLUESCRIPT clone was obtained using $^{35}$S-dideoxy sequencing kit (Amersham-Pharmacia Biotech, Piscataway, N.J.) and PCR fluorescence dye terminator kit (Applied. Biosystems, Foster City, Calif.). The non-radioactive sequencing reactions were analyzed on a ABI 373 sequencer. The complete DNA sequence was obtained by performing multiple reactions using both insert-specific and pBluescript-specific primers. Sequence compilation and identification of open reading frames for the recombinant clones were performed using the GCG sequence analysis package.

DNA sequencing of bacteriophage clone rCP41 revealed an insert of 740 nt in length, containing an open reading frame (ORF) that was in-frame with beta-galactosidase of lambda ZAP/pBluescript (FIG. 2). Two potential ATG start sites were identified; one at nt 139, the other at nt 196. Both sites conform to the Kozak consensus sequence for translation initiation at the −3 and +4 nt position.

EXAMPLE 8

Production of Recombinant Poly-histidine Proteins

The Cryptosporidium insert DNA was excised from pBluescript by PstI and HindIII digestion and ligated into the pTrcHis A vector (Invitrogen, Carlsbad, Calif.) cut with the same restriction enzymes. Recombinant plasmid DNA was introduced into *Escherichia coli* DH5 cells using standard transformation procedures. Maintenance of the open reading frame between pTrcHis and the insert DNA was confirmed by DNA sequencing. A time-course study to identify the time of IPTG induction for peak expression of recombinant protein indicated that 4 hr induction was optimal.

Immunoblots of SDS-PAGE fractionated protein extracts from *E. coli* harboring recombinant pTrcHis-CP41 plasmid contained two unique protein bands, 28 and 36 kDa, produced 4 hr after IPTG induction (FIG. 1). Protein extracts from *E. coli* harboring non-recombinant pTrcHis plasmid contained neither the 28 nor the 36 kDa recombinant protein (data not shown). Purification of rCP41 by NiNTA affinity chromatography showed that only the 36 kDa protein was isolated (FIG. 1). The 28 kDa and 36 kDa recombinant CP41 proteins were excised from unlabeled membrane and subjected to N-terminal amino acid sequencing (Beckman Center, Stanford University Medical Center, Palo Alto, Calif.). The 36 kDa protein appeared to be the actual fusion protein containing pTrcHis-encoded amino acids at its N-terminus. The amino acid sequence of the recombinant 28 kDa protein indicated that in *E. coli*, translation also initiated from the CP41 start codon at nt 196.

EXAMPLE 9

Production of Antisera Against Recombinant PolyHis-CP41 Fusion Proteins

New Zealand White rabbits (Covance) were immunized three times over a two month period with 28 kDa and 36 kDa recombinant CP41 proteins impregnated on nitrocellulose paper which had been ground in a mini-mortar and pestle similar to the procedure described above. The rabbits were bled for serum by central auricular artery puncture 2 weeks after the last booster immunization.

EXAMPLE 10

Characterization of Recombinant PolyHis-CP41 Fusion Proteins

In immunoblot assays, antisera against the 36 kDa recombinant protein recognized a native 41 kDa *C. parvum* antigen (FIG. 1). A similar pattern was observed with antisera against the 28 kDa recombinant protein (data not shown). Antisera raised against native or recombinant CP41 antigen showed a similar pattern in immunoblots with whole native *C. parvum* oocyst protein (Cp), purified (P) or unpurified (IP) recombinant CP41 protein (FIG. 1). Normal control serum showed negligible recognition of native *C. parvum* protein or purified recombinant CP41 antigen (FIG. 1). A band similar in size to the recombinant CP41 antigen was present in unpurified recombinant protein extracts and recognized by normal control serum (FIG. 1).

The relationship between native and recombinant CP41 proteins was unknown except that these antigens share at least one common epitope. The size discrepancy between the native CP41 protein and either the 36 kDa or the 28 kDa recombinant CP41 proteins did not appear to be due to glycan residues on the native protein. Glycosidase treatment was performed on total oocyst extracts to determine if CP41 was glycosylated. In addition, untreated SDS-PAGE-fractionated *C. parvum* protein impregnated on Immobilon membrane was treated with sodium periodate to remove glycan residues. No difference in molecular weight or intensity of immunoreaction was observed between treated and untreated protein samples (data not shown). The results indicated that native CP41 was not heavily glycosylated and that epitopes recognized by sera against native or recombinant CP41 protein did not involve glycan moieties.

Perhaps rCP41 is not a full-length clone, missing upstream and/or downstream coding sequences. The absence of a stop codon in the DNA sequence supports this hypothesis. The predicted size of the recombinant protein based on the pTrcHis fusion peptide (4 kDa) and the CP41 DNA sequence is 31 kDa. The predicted size of the recombinant protein initiating from the ATG at nt 196 is 19.5 kDa. The size discrepancy between either the predicted size of the full-length fusion protein (31 kDa) or the predicted truncated protein initiating at the internal ATG start site (19.5 kDa) and the observed 36 and 28 kDa recombinant proteins may be due to the previously reported aberrant migration of *E. coli*-expressed recombinant proteins in SDS-PAGE for proteins with atypical amino acid compositions. The CP41 coding sequence contains a disproportionate number of Asn (21%) and Thr (11%) residues representing almost one-third of the amino acids. The recombinant protein initiating from the internal ATG start site contains an even greater percentage of Asn (27%) and Thr (14%).

EXAMPLE 11

Immunofluorescence (IFA) Assays

*C. parvum* sporozoites were first excysted by treating oocysts with 1% sodium hypochlorite (20% Clorox) for 10 min. at room temperature (RT), washing 5 times with Hank's balanced salt solution (HBSS), resuspension in HBSS, and incubating for 1 hr in a humidified chamber at 37° C. in 5% $CO_2$. For examination by immunofluorescence microscopy, the excysted oocyst/sporozoite mixture was pipetted onto multi-well glass slides at $10^4$ oocysts per well (based on pre-excystation counts) and allowed to air dry at room temperature (RT). The parasites were then treated with PBS containing 1% bovine serum albumin (PBS-BSA) for 1 hr at RT followed by incubation with a 1:100 dilution of anti-CP41 or anti-rCP41 antisera in PBS-BSA for 2 hr at RT in a humidified chamber. Antibody binding was detected by treatment with FITC-labeled anti-rabbit IgG (H+L ch. Sp., Sigma Chemical Co.) for 1 hr at RT in a humidified chamber. The slides were washed by 3 separate immersions in PBS after each incubation step. After the last incubation, the slides were allowed to air dry, overlaid with several drops of VectaStain anti-bleaching mounting medium (Vector Laboratories) and a coverslip.

Figure 5A:
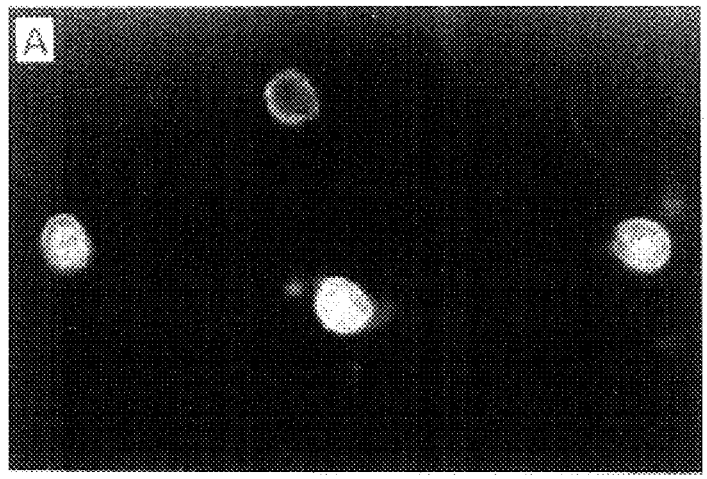
FIG. 5 shows the immunofluorescence staining of Cryptosporidium parvum oocysts with rabbit antisera prepared against native CP41 protein (A), or recombinant CP41 antigen (B), or with normal control rabbit sera (C).
Figure 5B:
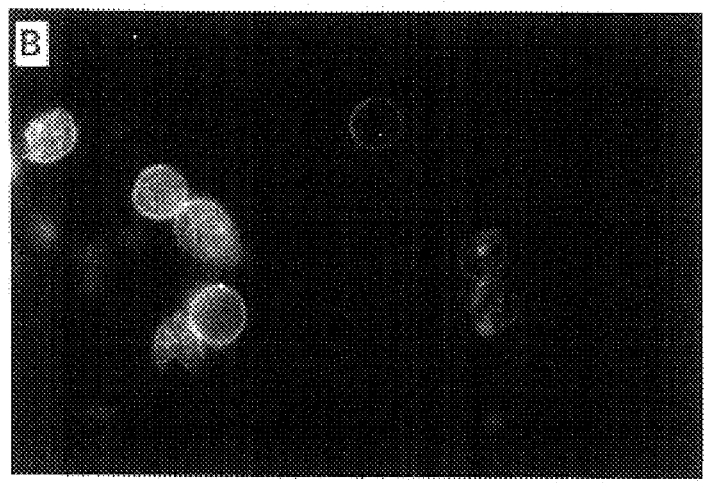
Figure 5C:

The *C. parvum* oocysts/sporozoites were examined on an epifluorescence microscope. Antisera to native or recombinant CP41 antigen bound a surface antigen of *C. parvum* oocysts (FIG. 5). Although not evident from the IFA figures, the target antigen appeared to be distributed unevenly on the surface of the oocyst. Negligible staining of *C. baileyi* oocysts was observed with antisera to native or recombinant CP41 antigen (data not shown).

EXAMPLE 12

Immunoelectron Microscopy (IEM) Assays

For IEM, the excysted sporozoite/oocyst mixture was washed several times in PBS, enumerated on a hemocytometer, aliquoted at $10^8$ sporozoites into 1.5 ml microcentrifuge tubes, and pelleted by centrifugation. The oocyst/sporozoite pellet was resuspended in 2% paraformaldehyde, 0.5% glutaraldehyde in 0.1M sodium cacodylate for 20 min. at RT. The fixed parasites were washed twice with 0.1M sodium cacodylate and pelleted by centrifugation. The oocyst/sporozoite pellet was dehydrated in a graded ethanol series, infiltrated overnight in LR White hard grade acrylic resin, and cured at 55° C. for 24 hr. Thin sections (90 nm) were obtained using a Diatome diamond knife on a Reicher/AO ultracut microtome and collected on 200-mesh nickel grids. The grids were floated on drops of PBS containing 0.1M glycine and 1% BSA for 10 min, washed with PBS, floated on drops of PBS-NFDM-Tw20, and floated on drops of PBS containing 1:100 dilution of normal goat serum. The grids were incubated on drops containing a 1:100 dilution of rabbit antisera (anti-CP41 or anti-rCP41) in PBS-NFDM-Tw20 in a humidified chamber. The grids were incubated for 2 hr at RT, washed three times with PBS-Tw20-NFDM, and floated for 1 hr at RT on drops of a 1:100 dilution of gold-labeled (10 nm) goat anti-rabbit IgG (H+L ch. sp., Vector Laboratories). The grids were washed three times with PBS-Tw20, once with distilled water, air-dried, and stained with 5% uranyl acetate for 30 min.

Figure 6A:
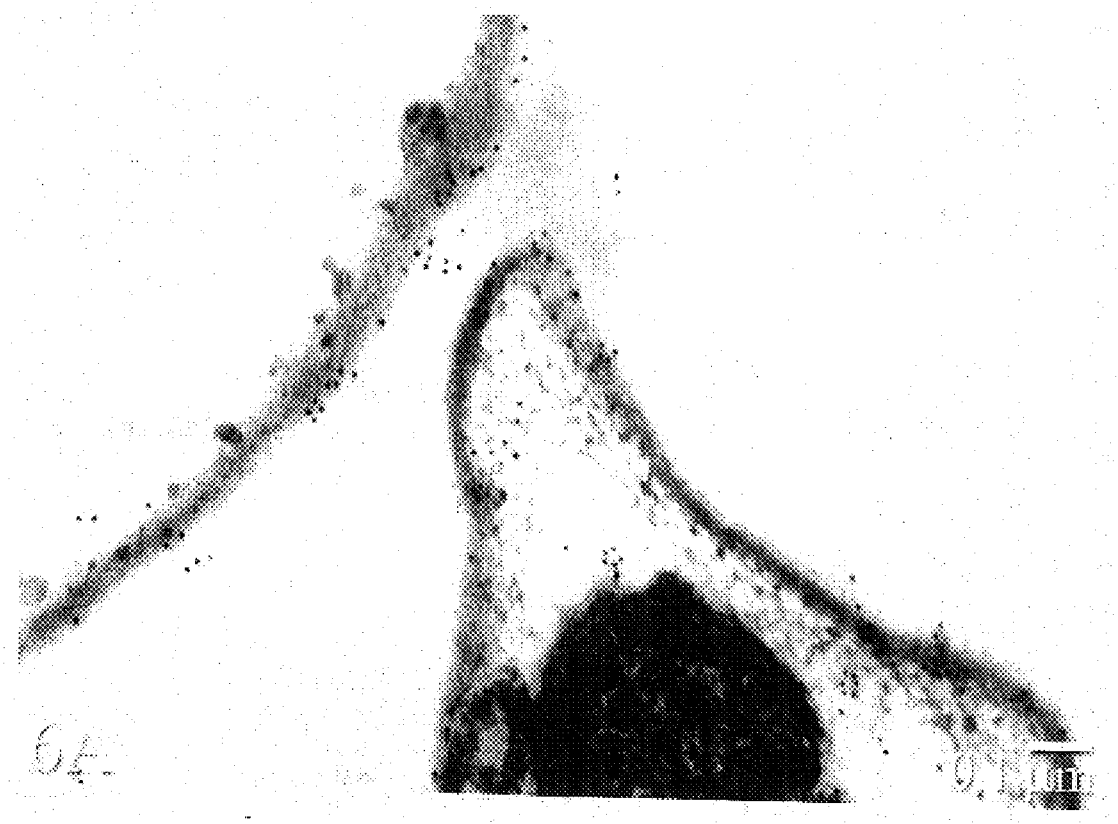
FIG. 6 shows immunoelectron microscopy staining of *Cryptosporidium parvum* oocysts with rabbit antisera prepared against native CP41 protein (A), or recombinant CP41 antigen (B). Bar=100 nm.
Figure 6B:
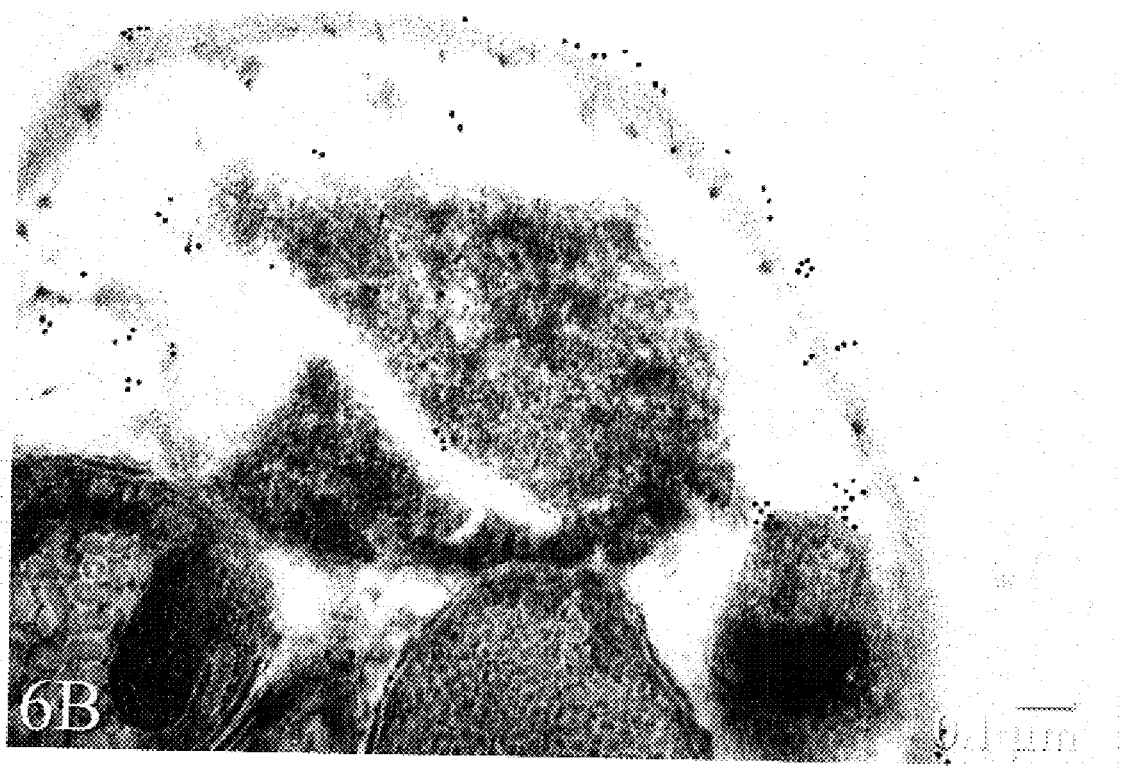

Grids were examined on a Hitachi H500H transmission electron microscope at 75 kV. The surface location and distribution of CP41 antigen observed by IFA was confirmed by IEM (FIG. 6). The antigen was present on both external and internal regions of the oocyst wall and was also associated with amorphorous material on the oocyst outer surface.

EXAMPLE 13

Preparation of Primers

Figure 3:
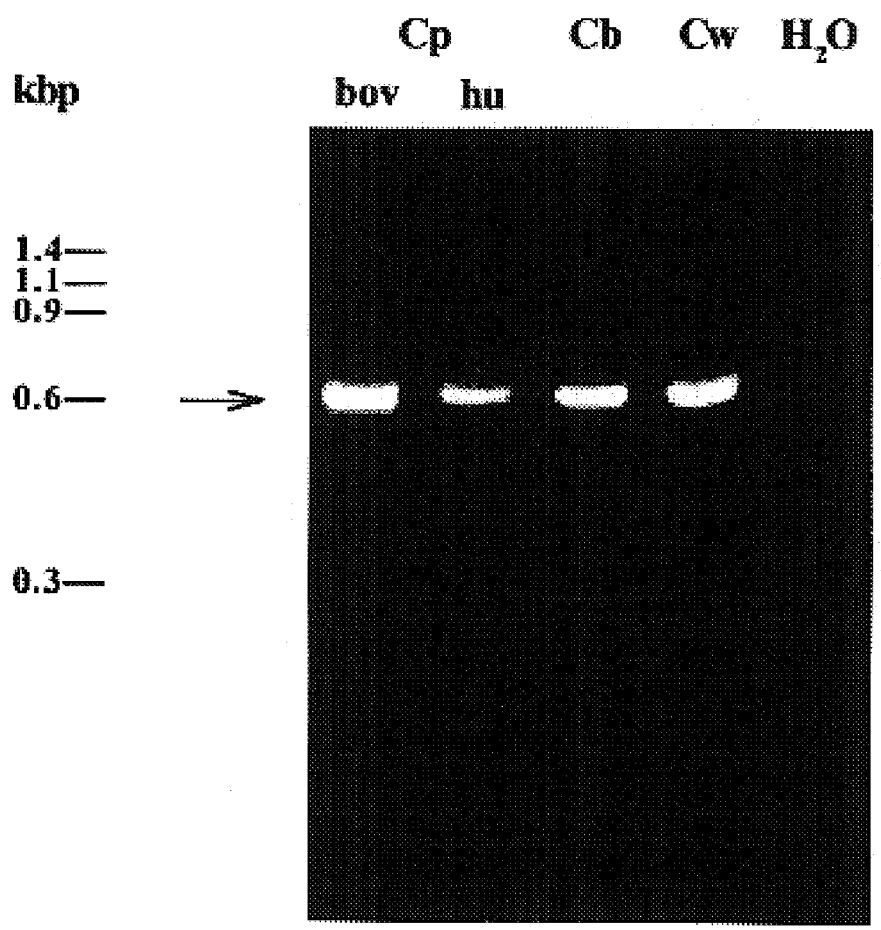
FIG. 3 shows PCR amplification of the CP41 sequence from genomic DNA (equivalent to $10^3$ oocysts) from a bovine isolate of Cryptosporidium parvum (Cp-bov), a human isolate of C. parvum (Cp-hu), C. baileyi (Cb), or C. wrairi (Cw). Kbp, φx174 DNA standards.
Figure 4:
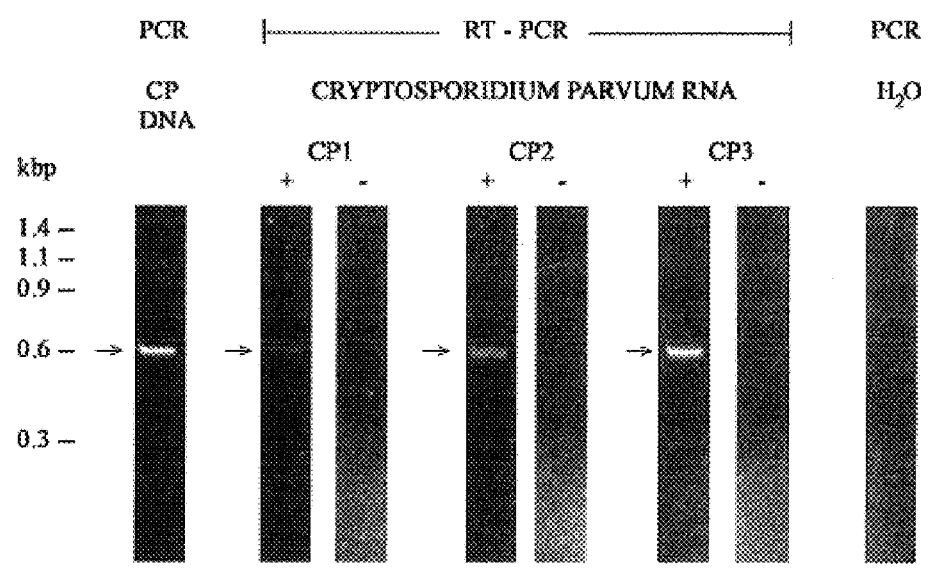
FIG. 4 shows the molecular analysis of Cryptosporidium parvum for presence of CP41 sequence in genomic DNA using PCR, and for CP41 mRNA in total RNA using RT-PCR. The PCR assay was performed on DNA equivalent to $10^3$ C. parvum oocysts (CP DNA). The RT-PCR was performed on total RNA equivalent to $5 \times 10^5$ C. parvum oocysts stored at 4° C. for 6 mo. (CP1), 3 mo. (CP2), or 1 mo. (CP3). +, Superscript reverse transcriptase (Rtase) added to first step cDNA synthesis reaction; −, no Rtase added to first step cDNA synthesis reaction. Kbp, φx174 DNA standards.

The oligonucleotide primers CP41F, 5'-AGCATTAGTAGCAACAGTAG-3'(SEQ ID NO:3) and CP41 R, 5'-GAGATGGACTATTCTAGG-3'(SEQ ID NO:4) were prepared based on the rCP41 DNA sequence. The CP41F and CP41 R primers were used in PCR to amplify the respective sequence in genomic DNA from two *C. parvum* isolates, *C. baileyi*, and *C.wrairi*. An amplification product similar in size to the insert DNA was observed, indicating that rCP41 was present in *C. parvum* (bovine and human isolates), *C. baileyi*, and *C. wrairi* genomic DNA (FIG. 3).

EXAMPLE 14

Reverse Transcriptase-polymerase Chain Reaction (RT-PCR) Analysis of *Cryptosporidium parvum* Oocyst RNA

*C. parvum* oocysts stored for 1, 3, or 6 mos. at 4° C. were analyzed for the presence of CP41 messenger RNA using RT-PCR. First strand cDNA synthesis from 1 μg total *C. parvum* RNA was carried out at 42° C. in reaction buffer containing 20 U Superscript II reverse transcriptase (Gibco-BRL), and either 2 pmole of a gene-specific CP41-F1 primer (5' AGCATTAGTAGCAACAGTAG 3', SEQ ID NO:3) or 4 pmole oligo dT primer in a total volume of 20 μl of first strand reaction mixture, 0.25 U Taq polymerase (Gibco-BRL), and 50 pmole of CP41-F1 and CP41-R1 (5'GAGATGGACTATTCTAGG 3', SEQ ID NO:4) primers in a final volume of 50 μl. Amplification was performed on a Stratagene Robocyler using the following PCR amplification cycles: denaturation, 94° C., 1 min; annealing, 55° C., 1 min; extension, 72° C., 2 min., for 30 cycles followed by a final extension at 72° C. for 2 min. To analyze for the presence of CP41 in genomic DNA, a single PCR was performed on DNA equivalent to $10^3$ Cryptosporidium oocysts using reaction conditions identical to those described above. The PCR products were analyzed by polyacrylamide gel electrophoresis, EtBr staining and UV transillumination followed by capture to a CCD camera as described (Jenkins et al. 1998. *J. Parasitol.* 84: 182–186).

RT-PCR on total RNA showed that the CP41 transcript was present in *C. parvum* oocysts (FIG. 4). Although equivalent amounts of total RNA were used in each reaction, the intensity of the RT-PCR signal appeared to be inversely correlated with the age of *C. parvum* oocysts. The RT-PCR signal derived. from RNA isolated from oocysts that had been stored at 4° C. for 6 mo (CP1+) or 3 mo (CP2+) was about 25% and 50%, respectively, of the signal obtained from 1 mo old oocysts (CP3+, FIG. 3). The control reactions in which reverse transcriptase was not included did not show a PCR product indicating that the RT-PCR signal was due to the presence of mRNA rather than contaminating DNA (CP1−, CP2−, CP3−; FIG. 3). In RT-PCR assays on *C. baileyi* RNA, CP41 messenger RNA was not detectable (data not shown); RT-PCR could not be performed on *C. wrairi* because RNA from this species was not available. Attempts to identify the transcript size in *C. parvum* by Northern blot hybridization assay were unsuccessful.

EXAMPLE 15

Enzyme-linked Immunosorbent Assay (ELISA)

Antisera were obtained weekly beginning at one day of age, for 7–10 weeks from 4 calves that had been given normal bovine colostrum (NBC) at birth and housed in a dairy operation that had experience sporadic outbreaks of cryptosporidiosis (natural infection). The calves were examined daily for diarrhea and excretion of *C. parvum* oocysts in feces using standard methods. Antisera was also obtained from a calf prior to and every week for one month after being fed NBC at birth and inoculated per os with $10^6$ *C. parvum* oocysts (experimental infection). Antisera were also obtained from adult cows (3–4 years old) before and for several weeks after experimental *C. parvum* challenge and from two adult cows that had not been exposed to *C. parvum*. Antisera were tested by ELISA for recognition of native *C. parvum* oocyst protein and recombinant CP41 antigen. In the former, *C. parvum* oocysts were subjected to multiple freeze-thaw cycles and disruption on a Mini-bead beater (Bespeak Products, Bartlesville, Okla.) followed by centrifugation to pellet insoluble material. The oocyst protein supernatant (50 μl), equivalent to $4 \times 10^4$ oocysts (150 ng protein), was pipetted onto individual wells of Immulon II microtiter plates and incubated overnight at 4° C. Native *C. parvum* protein ELISA was performed as previously described (Harp et al. 1989. *Am. J. Vet. Res.* 50: 2117–2119). Titers are given as the reciprocal of the highest dilution giving an absorbance reading twice that of the average reading for the 1:80 dilution of the negative control serum. Recombinant CP41 poly-histidine fusion protein was purified by denaturing NiNTA affinity chromatography according to manufacturer's directions (Invitrogen). Eluates containing peak amounts of purified protein as indicated by SDS-PAGE/immunoblotting were pooled and adsorbed to the surface of Immulon II microtiter plates as described above. The wells were washed with PBS to remove unbound recombinant antigen and then treated with PBS containing 2% normal horse serum (Sigma Chemical Co. For 1 hr at RT to inhibit non-specific Ab binding in subsequent incubation steps. The wells were washed with PBS-Tw20 and then incubated for 2 hr at RT with 100 µl serial dilutions of positive control bovine sera or a 1:100 dilution of negative control bovine serum or sera from calves or cows as described above. After washing 3 times with PBS-Tw20, the wells were incubated with 100 µl of a 1:1000 dilution of peroxidase-labeled goat anti-bovine IgG (H+L ch. sp., Sigma Chemical Co.) for 1 hr at RT. The wells were washed 3 times with PBS-Tw20 and incubated for 10 min. with 50 µl peroxidase substrate (0.01 mg/ml o-phenylene diamine, 0.001% $H_2O_2$ in PBS). Color development was stopped by the addition of 50 µl 2% $H_2SO_4$ to each well. The absorbance at 492 nm was read on a BioRad model 450 micro plate reader. The titer of anti-recombinant CP41 antigen Ab in serum was estimated through use of the standard curve generated from the positive control serum using described procedures (Jenkins et al. 1997. *Clin. Diag. Lab. Immunol.* 4: 270–274).

Figure 7A:
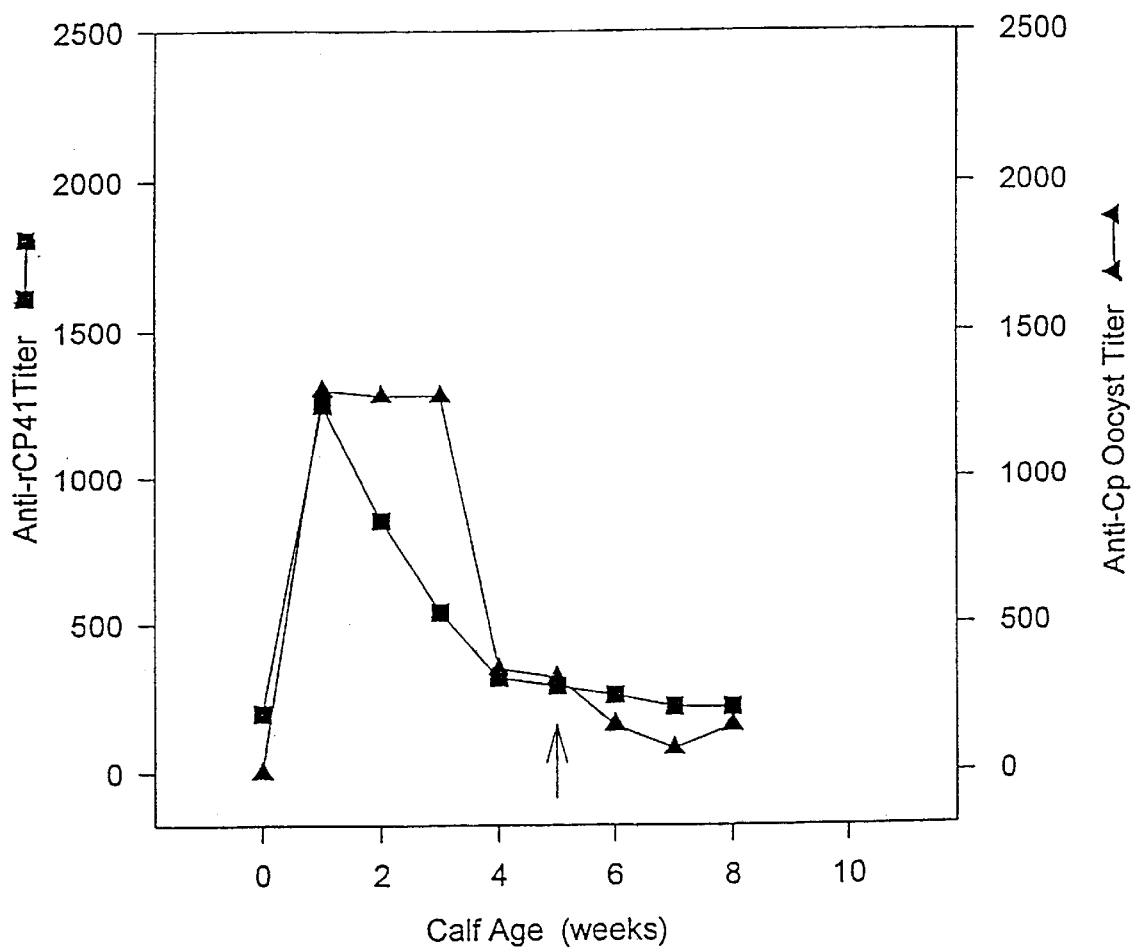
FIG. 7 shows serological titers against recombinant CP41 (■--■) and native *Cryptosporidium parvum* oocyst protein (▲--▲) in four calves (A-D) exposed to a natural *C. parvum* infection and one calf (E) exposed to an experimental natural *C. parvum* infection as revealed by ELISA. Arrow indicates first day of *C. parvum* oocyst shedding.
Figure 7B:
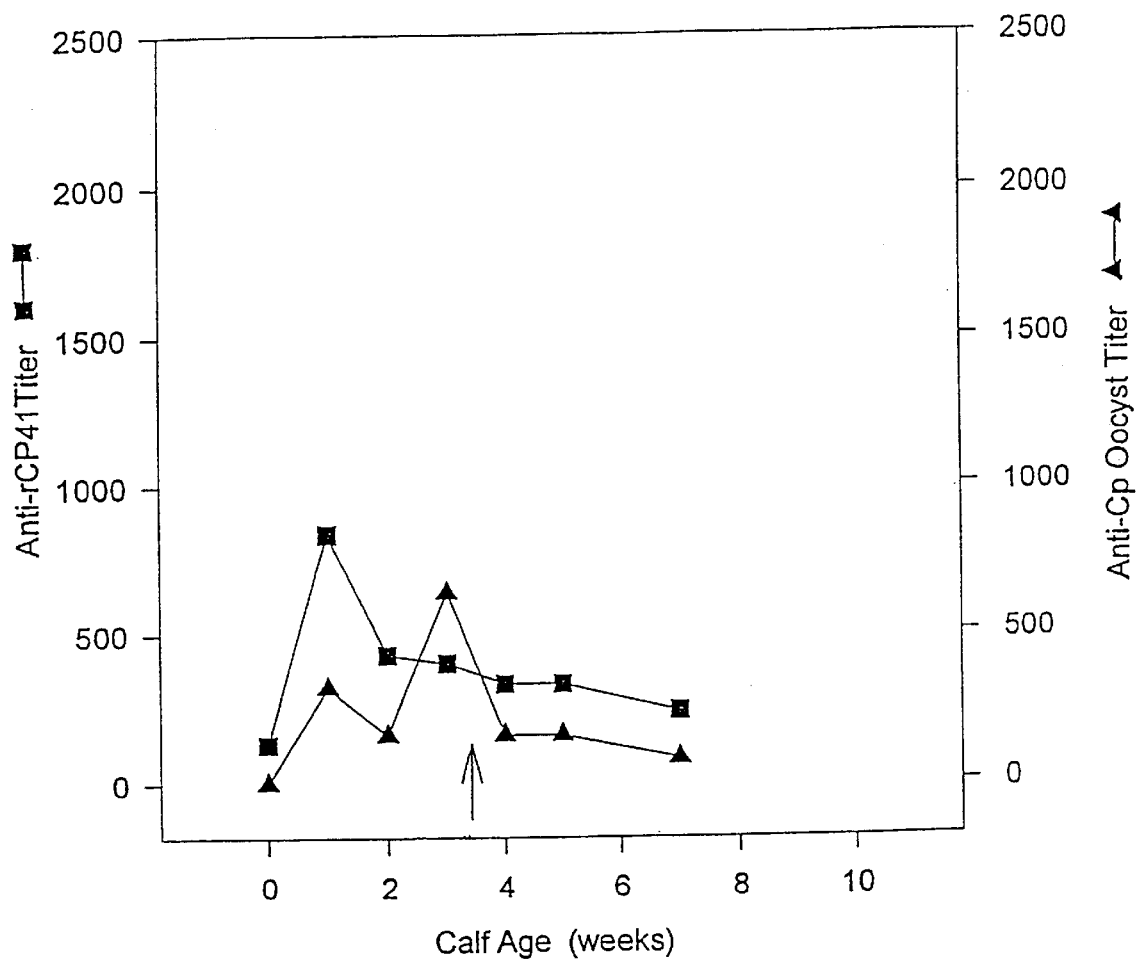
Figure 7C:
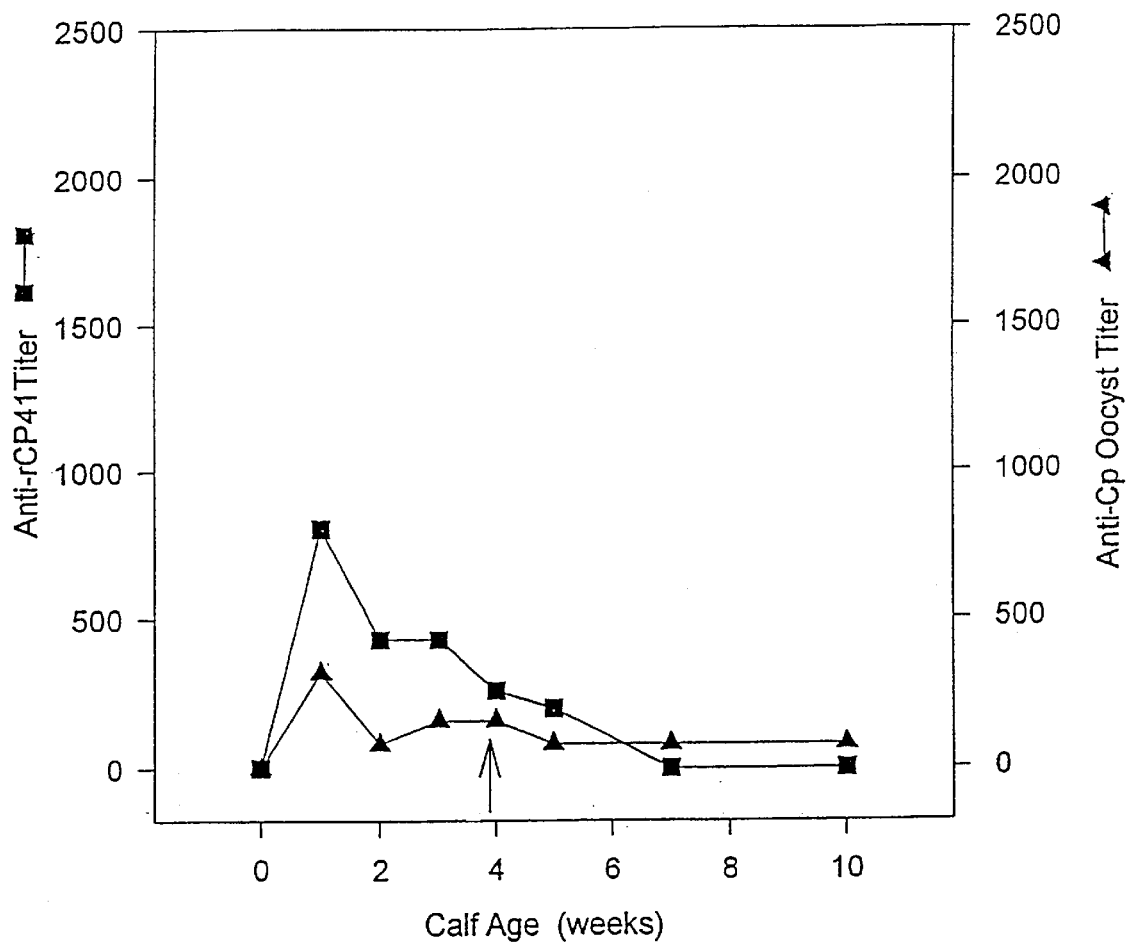
Figure 7D:
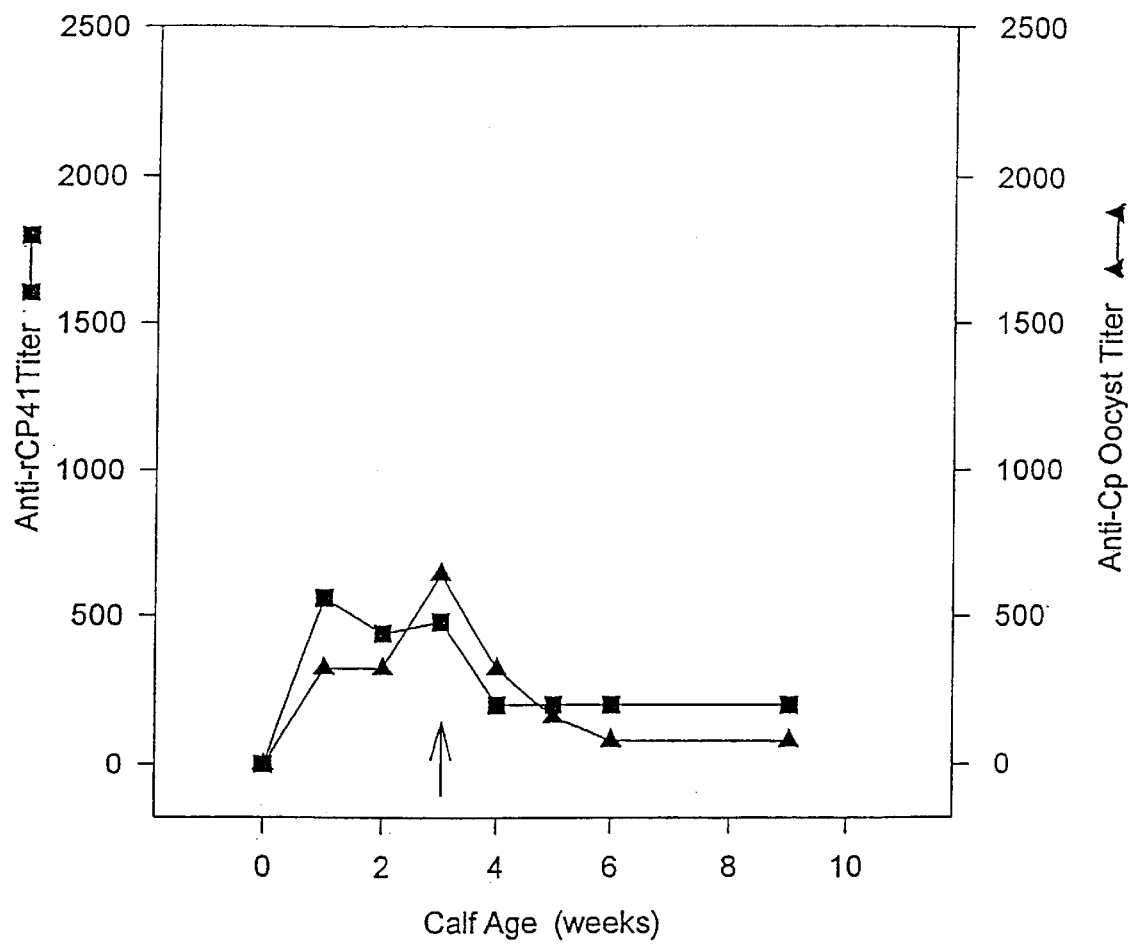
Figure 7E:
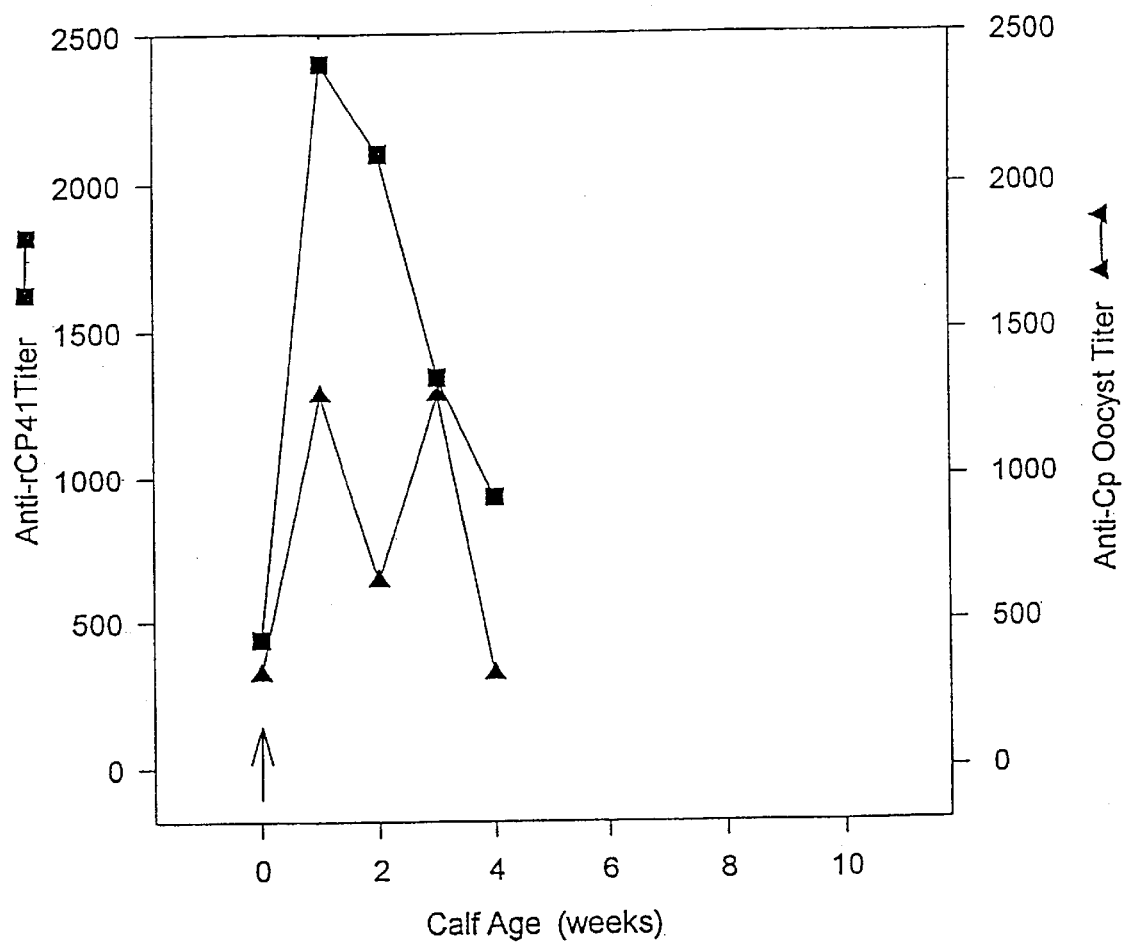

Recombinant CP41 antigen showed levels of binding similar to native *C. parvum* oocyst antigen when probed with sera from adult cows that were exposed to *C. parvum* (Table 1). The pre-infection titers to both native and recombinant antigens were high and did not appear to increase appreciably after experimental challenge. Perhaps boosting of the antibody response was not observed because oocyst challenge did not result in patent infection due to the age-related resistance of adult cows to *C. parvum* infection. In young calves exposed to a natural *C. parvum* infection, titers to recombinant CP41 antigen were high at the first post-colostral bleeding, possibly due to the presence of anti-CP41 antibodies in normal colostrum, and then decreased (FIGS. 7A–7D). No increase in Ab titers to rCP41 was noted after exposure to *C. parvum*. The Ab titers to native *C. parvum* oocyst antigen were variable. In two calves (FIGS. 7B,7D), the highest titers against native antigen occurred at time of oocyst shedding. In the other two calves, peak anti-*C. parvum* antigen titers were observed immediately after colostrum feeding (FIGS. 7A, 7C). A similar pattern was observed after an experimental *C. parvum* infection of a one-day-old calf (FIG. 7E). Antibody titers to rCP41 and native *C. parvum* oocyst antigen were highest after colostrum feeding and natural *C. parvum* oocyst inoculation (FIG. 7E). Although anti-rCP41 titers decreased with time, the response to native *C. parvum* oocyst titers was variable (FIG. 7E).

TABLE 1

Anti-recombinant Cp4l and native Cryptosporidium parvum oocyst antigen titers in sera from adult cows after experimental cryptosporidiosis infection or in unexposed control adult cows.

| Cow No. Experimental Infections: | Time Post-infection (wk) | ELISA Titer rCP41 | nCP oocyst |
|---|---|---|---|
| 1 | 0 | 1100 | 2560 |
|  | 1 | 1310 | ND* |
|  | 2 | 1200 | 1280 |
|  | 3 | 1200 | 2560 |
|  | 4 | 1110 | 2560 |
| 2 | 0 | 900 | 2560 |
|  | 1 | 1020 | ND |
|  | 2 | 1260 | 1280 |
|  | 3 | 1070 | 2560 |

TABLE 1-continued

Anti-recombinant Cp4l and native Cryptosporidium parvum oocyst antigen titers in sera from adult cows after experimental cryptosporidiosis infection or in unexposed control adult cows.

| Cow No. Experimental Infections: | Time Post-infection (wk) | ELISA Titer rCP41 | nCP oocyst |
|---|---|---|---|
| 3 | 0 | 890 | ND |
|  | 1 | 850 | 1280 |
|  | 2 | 900 | 2560 |
|  | 3 | 1200 | 5120 |
| Unexposed Controls: |  |  |  |
| 1 |  | <100 | <100 |
| 2 |  | <100 | 320 |

*ND, not done

EXAMPLE 16

Generation of Monoclonal Antibodies
Immunization of mice and hybridization of splenocytes with cells of the myeloma line SP2-01/Ag.14 (ATCC CRL 1581)

BALB/c mice were immunized twice (Day 1 and Day 30) with rCP41 antigen impregnated on nitrocellulose membrane and then boosted intravenously two weeks later with soluble rCP41 antigen. Three days following the intravenous immunization, the spleen was harvested and fused with the SP0 myeloma cell line. HAT selection (Boehringer Mannheim, Indianapolis, Ind.) was begun 24 hrs after the fusion. Hybridoma supernatants were screened by ELISA using rCP41 antigen and by immunofluorescence assay using *C. parvum* oocysts dried to the surface of multi-well glass slides. Cloning by limiting dilution was performed until a single clone was observed in a microtiter well and only one immunoglobulin isotype was present. Reactive clones were confirmed dat each step of the cloning process by ELISA and IFA.

EXAMPLE 17

Immunization Experiments with pCMV-CP41 Plasmid DNA

Preparturient dairy cows (n=2) were immunized at 6, 4, and 2 weeks prior to parturition with 1.0 mg pCMV-CP41 plasmid preparation. This plasmid contains a CMV promoter sequence upstream of the CP41 DNA sequence and is capable of expressing CP41 protein in eukaryotic cells. At each time-point, the cows were bled for serum and then given an intramammary injection with pCMV-CP41 plasmid DNA via needle and syringe. Colostrum and serum from the dam was collected within 24 hr after birth of the calf. The sera from each time-point and colostrum were assayed for antibodies to recombinant CP41 antigen by ELISA. Unlike pre-immunization sera, a high titer anti-rCP41 response was observed in sera from cows immunized with pCMV-CP41 plasmid DNA as early as 4 weeks post-primary immunization. In addition, colostrum from cows immunized with pCMV-CP41 plasmid DNA contained a high titer of antibodies against rCP41 compared to colostrum from normal control cows. These data indicate that CP41 can be expressed under control of a CMV promoter and that high titer anti-rCP41 antibody responses in sera and colostrum from cows immunized with pCMV-CP41 can be achieved.

It is understood that the foregoing detailed description is given merely by way of illustration and that modifications and variations may be made therein without departing from the spirit and scope of the invention.

We claim:

1. An isolated rCP41 protein comprising the amino acid sequence of SEQ ID NO: 2.

2. An isolated portion of rCP41 protein comprising one or more epitopes of rCP41 protein wherein said rCP41 protein comprises an amino acid sequence shown in SEQ ID NO:2 and wherein said portion is antigenic and effective to elicit an immune response against *Cryptosporidium parvum* in a host animal.

3. A rCP41 fusion protein comprising one or more epitopes of rCP41 protein wherein said rCP41 protein comprises an amino acid sequence shown in SEQ ID NO:2 and wherein said protein is antigenic and effective to elicit an immune response against *Cryptosporidium parvum* in a host animal, operably coupled to another unrelated polypeptide sequence.

4. The protein according to any one of claims 1, 2, and 3, wherein said protein is produced by recombinant methods.

5. A composition comprising the protein of any one of claims 1, 2, and 3 and a pharmaceutically acceptable carrier.

* * * * *

SEQUENCE LISTING

<160> NUMBER OF SEQ ID NOS: 4

<210> SEQ ID NO 1
<211> LENGTH: 740
<212> TYPE: DNA
<213> ORGANISM: Cryptosporidium parvum

<400> SEQUENCE: 1

```
aatttcttct tttatgatga ttctaaaaag tatgagggag gattattaaa aaaagaaggt    60
tatgatggtt gtacagtagt tggtagtgat tgtttatgtt ggagatgtta tttcaatcaa   120
agaccatttt ttgaggagat ggactattct aggattccaa tttcttctga ggttatttgt   180
ggattattga atggaatgga atattgtatt tgtaaatgtg atgaattgga tatattatta   240
gaaagatgga atccattttt gctttataaa tttgagcagg aatatttaaa gaatggagca   300
attttaatgg ataataatat tggaatactt gtaaataata caatggtagg tattggtaaa   360
aggatgaata ctactcaatc aatggaagtt actgatacta atattggtaa tatgagtggt   420
attattacat ctagtggtga ttctatagct gttactaata atcttaatgg taataataat   480
agtaatagta atattggatc aggaaatttt ataccagttg gtacttgttc ttctactagt   540
attggtaata gtaatggtgt tgcttttact gctattcatc ctaataataa caatagcaat   600
aatattaata ataataataa taataatagt aataccactc ttactactgt tgctactaat   660
gctaatatta ctactaatac tactaatact actactacta ctactaataa taataataat   720
aataataata ataataattc                                                740
```

<210> SEQ ID NO 2
<211> LENGTH: 246
<212> TYPE: PRT
<213> ORGANISM: Cryptosporidium parvum

<400> SEQUENCE: 2

```
Asn Phe Phe Tyr Asp Asp Ser Lys Lys Tyr Glu Gly Gly Leu Leu
  1               5                  10                  15

Lys Lys Glu Gly Tyr Asp Gly Cys Thr Val Val Gly Ser Asp Cys Leu
                 20                  25                  30

Cys Trp Arg Cys Tyr Phe Asn Gln Arg Pro Phe Phe Glu Glu Met Asp
             35                  40                  45

Tyr Ser Arg Ile Pro Ile Ser Ser Glu Val Ile Cys Gly Leu Leu Asn
         50                  55                  60

Gly Met Glu Tyr Cys Ile Cys Lys Cys Asp Glu Leu Asp Ile Leu Leu
 65                  70                  75                  80

Glu Arg Trp Asn Pro Phe Leu Leu Tyr Lys Phe Glu Gln Glu Tyr Leu
                 85                  90                  95

Lys Asn Gly Ala Ile Leu Met Asp Asn Asn Ile Gly Ile Leu Val Asn
            100                 105                 110

Asn Thr Met Val Gly Ile Gly Lys Arg Met Asn Thr Thr Gln Ser Met
            115                 120                 125

Glu Val Thr Asp Thr Asn Ile Gly Asn Met Ser Gly Ile Ile Thr Ser
        130                 135                 140

Ser Gly Asp Ser Ile Ala Val Thr Asn Asn Leu Asn Gly Asn Asn Asn
145                 150                 155                 160

Ser Asn Ser Asn Ile Gly Ser Gly Asn Phe Ile Pro Val Gly Thr Cys
                165                 170                 175
```

-continued

```
Ser Ser Thr Ser Ile Gly Asn Ser Asn Gly Val Ala Phe Thr Ala Ile
            180                 185                 190

His Pro Asn Asn Asn Ser Asn Asn Ile Asn Asn Asn Asn Asn Asn
        195                 200                 205

Asn Ser Asn Thr Thr Leu Thr Thr Val Ala Thr Asn Ala Asn Ile Thr
    210                 215                 220

Thr Asn Thr Thr Asn Thr Thr Thr Thr Thr Thr Asn Asn Asn Asn Asn
225                 230                 235                 240

Asn Asn Asn Asn Asn Asn
                245

<210> SEQ ID NO 3
<211> LENGTH: 20
<212> TYPE: DNA
<213> ORGANISM: Cryptosporidium parvum

<400> SEQUENCE: 3
agcattagta gcaacagtag                                              20

<210> SEQ ID NO 4
<211> LENGTH: 18
<212> TYPE: DNA
<213> ORGANISM: Cryptosporidium parvum

<400> SEQUENCE: 4
gagatggact attctagg                                                18
```